(12) United States Patent
Boinagrov et al.

(10) Patent No.: US 11,998,268 B2
(45) Date of Patent: Jun. 4, 2024

(54) SYSTEM AND METHODS FOR TREATING SKIN

(71) Applicant: SCITON, INC., Palo Alto, CA (US)

(72) Inventors: David Boinagrov, Mountain View, CA (US); James L. Hobart, Palo Alto, CA (US); Daniel K. Negus, Palo Alto, CA (US); Hartmuth Hecht, Moss Beach, CA (US); Frank Garcia, Redwood City, CA (US)

(73) Assignee: Sciton, Inc., Palo Alto, CA (US)

( * ) Notice: Subject to any disclaimer, the term of this patent is extended or adjusted under 35 U.S.C. 154(b) by 100 days.

(21) Appl. No.: 16/614,640

(22) PCT Filed: May 18, 2018

(86) PCT No.: PCT/US2018/033407
§ 371 (c)(1),
(2) Date: Nov. 18, 2019

(87) PCT Pub. No.: WO2018/213716
PCT Pub. Date: Nov. 22, 2018

(65) Prior Publication Data
US 2021/0282855 A1      Sep. 16, 2021

Related U.S. Application Data

(60) Provisional application No. 62/508,568, filed on May 19, 2017.

(51) Int. Cl.
| A61B 18/20 | (2006.01) |
| A61B 17/00 | (2006.01) |
| A61B 18/00 | (2006.01) |

(52) U.S. Cl.
CPC .. *A61B 18/203* (2013.01); *A61B 2017/00761* (2013.01); *A61B 2017/00765* (2013.01);
(Continued)

(58) Field of Classification Search
CPC ........ A61B 18/203; A61B 2017/00761; A61B 2017/00765; A61B 2018/00458;
(Continued)

(56) References Cited

U.S. PATENT DOCUMENTS

| 2001/0016732 A1 | 8/2001 | Hobart et al. |
| 2007/0179481 A1 | 8/2007 | Frangineas et al. |

(Continued)

FOREIGN PATENT DOCUMENTS

WO      2015164923 A1      11/2015

OTHER PUBLICATIONS

International Searching Authority, International Search Report, Aug. 8, 2018.

*Primary Examiner* — Erin M Piateski
*Assistant Examiner* — Ranjani Mari Sundaresan
(74) *Attorney, Agent, or Firm* — Maynard Nexsen PC; John Zimmer; Nicholas Stadnyk

(57) ABSTRACT

In one aspect, a method of tightening skin and/or reducing scar tissue is described herein. The method comprises performing a fractional laser ablation in a treatment area of the skin, thereby removing a column of the skin and forming a columnar vacancy in the skin, the columnar vacancy having a perimeter defined by a first side and a second side opposite the first side, the first side and the second side each comprising an epidermal layer, a dermal layer, and a subcutaneous layer of skin. The first side of the columnar vacancy is contacted to the second side of the columnar vacancy, thereby closing the columnar vacancy.

15 Claims, 13 Drawing Sheets

(52) U.S. Cl.
CPC ............ *A61B 2018/00458* (2013.01); *A61B 2018/0047* (2013.01); *A61B 2018/00577* (2013.01); *A61B 2018/2015* (2013.01)

(58) Field of Classification Search
CPC .. A61B 2018/0047; A61B 2018/00577; A61B 2018/2015
See application file for complete search history.

(56) References Cited

U.S. PATENT DOCUMENTS

| | | | |
|---|---|---|---|
| 2014/0228731 A1* | 8/2014 | Jackson | A61F 13/00038 602/53 |
| 2015/0150629 A1* | 6/2015 | Anderson | A61B 17/0644 606/9 |
| 2016/0095592 A1 | 4/2016 | Levinson et al. | |
| 2016/0192961 A1 | 7/2016 | Ginggen et al. | |
| 2016/0317226 A1* | 11/2016 | Jagdeo | A61B 90/37 |

* cited by examiner

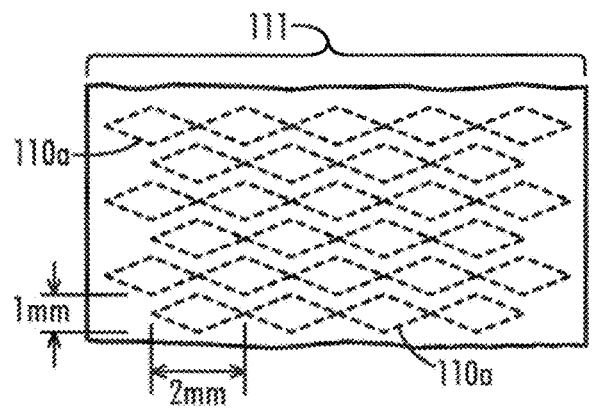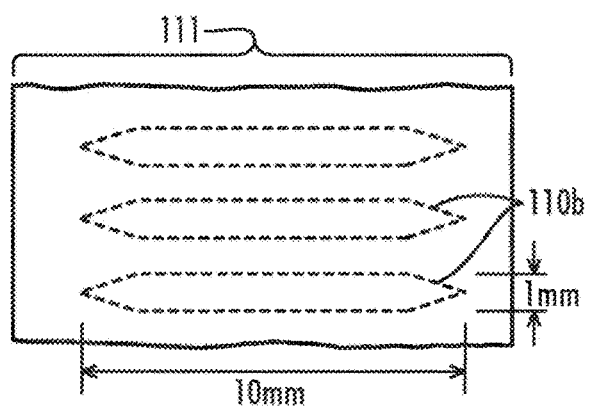
FIG. 5A    FIG. 5B
FIG. 6A
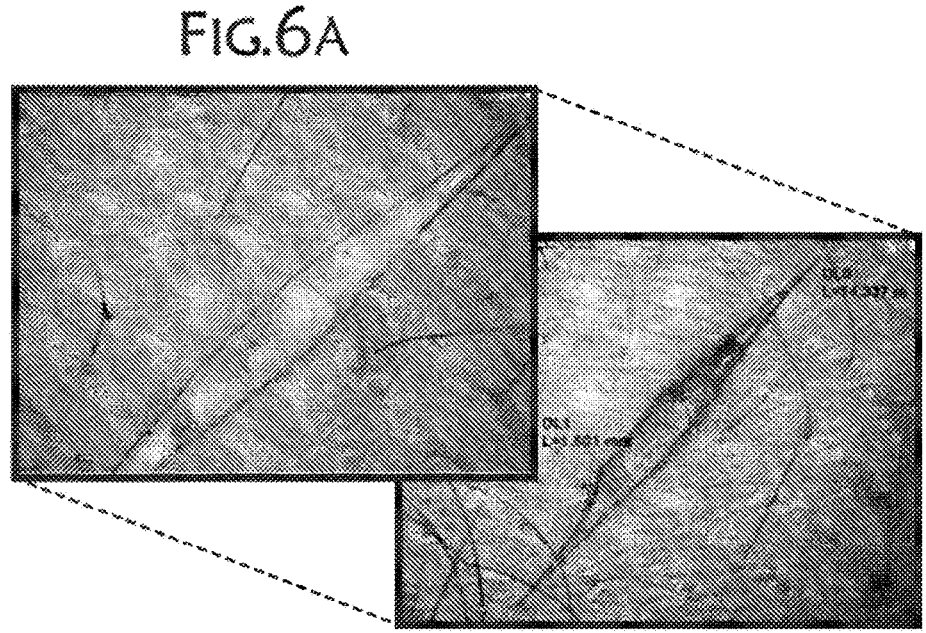
FIG. 6B

SYSTEM AND METHODS FOR TREATING SKIN

CROSS REFERENCE TO RELATED APPLICATIONS

This application is a U.S. National Phase of PCT/US2018/033407, files May 18, 2018, which claims priority pursuant to 35 U.S.C. §. 119 to U.S. Provisional Patent Application No. 62/508,568, filed on May 19, 2017, which are incorporated by reference herein in their entireties.

FIELD OF THE INVENTION

The invention is generally related to systems, devices, and methods for the treatment of skin, and, more specifically, to systems, devices, and methods of skin tightening, wound closure, and scar reduction and/or removal.

BACKGROUND

Scars are the result of the body's natural repair mechanisms after tissue injury. Scar severity is dependent on location, depth, and size of injury, with other contributing factors, such as age, genes, gender, and ethnicity (Fitzpatrick skin type). While scars are highly prevalent and often have a substantial negative impact on quality of life, efficacious scar treatment options are limited. Over-the-counter topical treatments have limited efficacy, while surgical excision can subsequently elicit additional scar formation.

Relatedly, excess skin can occur post weight loss, postpartum, following surgical procedures, after liposuction, or as a natural result of aging in the form of wrinkles. However, few or no minimally-invasive treatments exist to effectively remove unwanted excess skin.

Work in recent years has demonstrated the creation of scar-free skin incision techniques that remove unwanted or excess skin by making numerous incisions and contracting the edges. However, these techniques still have a number of drawbacks and limitations. For example, these techniques are not readily applicable to situations where numerous incisions are required, since manually performing numerous incisions is very tedious. Additionally, these techniques often require conventional suturing, which can lead to the formation of additional scars that need revision.

Consequently, improved systems and methods to remove excess skin or scar tissue and/or to tighten skin are needed.

SUMMARY

In one aspect, methods and systems for tightening skin or reducing scar tissue are described herein which, in some cases, can provide one or more advantages compared to other methods and systems. For example, in some embodiments, a method or system described herein can tighten skin on a subject by using fractional laser ablation to remove columns of skin. When a plurality of columns of skin are being removed, methods and devices described herein allow for an automated process, where a controller directs and guides the operation of the laser during fractional ablation. Moreover, methods and devices described herein can combine a laser with a blood vessel imaging system to remove columns of skin in low- or non-vascularized areas. The controller can be operatively connected to both the laser and the blood vessel imaging system, providing a method and system of automatively removing a plurality of columns of skin in the low or non-vascularized areas. In some embodiments, the removal of the columns of skin form columnar vacancies that are closed using an adhesive. Moreover, a method and system described herein can tighten skin or reduce scar tissue more efficiently and with better results compared to some other methods.

In one aspect, methods of tightening skin and/or reducing scar tissue are described herein. In some embodiments, such a method comprises removing a column of skin from a treatment area of the skin, thereby forming a columnar vacancy in the skin, the columnar vacancy having a perimeter defined by a first side and a second side opposite the first side, the first side and the second side each comprising an epidermal layer, a dermal layer, and a subcutaneous layer of skin. The method further comprises contacting the first side of the columnar vacancy to the second side of the columnar vacancy, thereby closing the columnar vacancy. Moreover, the epidermal layer, the dermal layer, and/or the subcutaneous layer of the first side of the columnar vacancy is aligned, respectively, with the epidermal layer, the dermal layer, and/or the subcutaneous layer of the second side of the columnar vacancy in a z-direction orthogonal to the surface of the skin.

In another embodiment, a method described herein comprises performing a fractional laser ablation in a treatment area of the skin, thereby removing a column of the skin and forming a columnar vacancy in the skin, the columnar vacancy having a perimeter defined by a first side and a second side opposite the first side, the first side and the second side each comprising an epidermal layer, a dermal layer, and a subcutaneous layer of skin. The first side of the columnar vacancy is contacted to the second side of the columnar vacancy, thereby closing the columnar vacancy.

Further, in some embodiments, an adhesive is applied to the skin over the closed columnar vacancy, such that the epidermal layer, the dermal layer, and/or the subcutaneous layer of the first side of the columnar vacancy is aligned, respectively, with the epidermal layer, the dermal layer, and/or the subcutaneous layer of the second side of the columnar vacancy in a z-direction orthogonal to the surface of the skin. In some instances, the adhesive applies a compressive force to the closed columnar vacancies.

In some embodiments, the columnar vacancy has an overall length and an overall width, the overall length being 2.5 to 3.5 times greater than the overall width.

In some embodiments, a method of tightening skin and/or reducing scar tissue described herein comprises imaging blood vessels in the treatment area prior to performing the fractional laser ablation, thereby forming a map of the vascularized and non-vascularized regions in the treatment area. In some cases, the fractional laser ablation is performed substantially on the non-vascularized regions based on the map of these vascularized and non-vascularized regions. In some embodiments, the laser is an Er:YAG laser.

In some embodiments, a plurality of columns of skin are removed during the fractional laser ablation, forming a plurality of columnar vacancies in the treatment area of the skin. In some instances the fractional laser ablation and imaging of blood vessels is automated. More particularly, in some cases, the automated fractional laser ablation and imaging of blood vessels is carried out using a computer controller operatively connected to a laser and an imager. The laser beam of the laser can have a polygonal, diamond-shaped, or ellipse-shaped cross-section. Particularly in some instances, the laser beam has an ellipse-shaped cross-section.

In some embodiments, methods for tightening skin or reducing scar tissue comprises the step of irradiating one or more closed columnar vacancies with a non-ablative laser or broad band light through an applied adhesive. In some instances, the irradiating causes hemostasis, coagulation, or both of the closed columnar vacancy.

Further, in some embodiments, the epidermal layers, the dermal layers, and the subcutaneous layers of the first and second sides of the columnar vacancy are aligned to form a substantially planar dermal-epidermal junction and a substantially planar dermal-subcutaneous junction across the first and second sides of the columnar vacancy when the columnar vacancies are closed.

In another aspect, system of skin tightening and/or scar tissue removal are described herein. In some embodiments, a system of skin tightening and/or scar tissue removal comprises a laser, an adhesive, and an imaging system. In some instances the laser is configured to fractionally ablate one or more columns of skin from a treatment area on the skin, thereby forming one or more columnar vacancies in the skin, the columnar vacancies each having a perimeter defined by a first side and a second side opposite the first side, the first side and the second side each comprising an epidermal layer, a dermal layer, and a subcutaneous layer of skin. In some embodiments, the adhesive is configured to be applied to the skin and apply compressive force to each columnar vacancy to hold the first side and second side of the columnar vacancy together. In some embodiments, the imaging system is configured to image blood vessels in the treatment area of the skin. In some cases, the imaging system determines locations of substantially non-vascularized areas within the treatment area of the skin based on the imaged blood vessels.

Additionally, in some instances, a system of skin tightening and/or scar tissue removal comprises one or more controllers operatively connected to the laser, the imaging system, or both. The one or more controllers are configured to automatedly control imaging of the blood vessels in the treatment area and fractional laser ablation locations in the treatment area. In some instances, the one or more controllers are configured to direct the laser to perform fractional ablation on the substantially non-vascularized skin in the treatment area.

In another aspect, methods of tightening skin and/or scar tissue removal are described herein. In some embodiments, such a method comprises attaching a frame, in an open position, to the surface of the skin, wherein the frame surrounds a treatment area of the skin. A column of skin is removed from a treatment area by ablating the skin with a laser, thereby forming a columnar vacancy in the skin, the columnar vacancy having a perimeter defined by a first side and a second side opposite the first side, the first side and the second side each comprising an epidermal layer, a dermal layer, and a subcutaneous layer of skin. In some instances, the method comprises altering the shape of the frame, while the frame is attached to the surface of the skin, from an open shape of the open position of the frame to a closed shape of a closed position of the frame, wherein altering the shape of the frame from the open shape to the closed shape connects the first side of the columnar vacancies to the second side of the columnar vacancy, and wherein the epidermal layer, the dermal layer, and/or the subcutaneous layer of the first side of the columnar vacancy is aligned, respectively, with the epidermal layer, the dermal layer, and/or the subcutaneous layer of the second side of the columnar vacancy in a z-direction orthogonal to the surface of the skin, when the frame is in the closed position.

Further, in some embodiments, the method of tightening skin and/or scar tissue removal comprises retaining the frame in the closed position on the surface of the skin during healing of the columnar vacancy; and removing the frame from the surface of the skin following healing of the columnar vacancy. In some instances, the frame comprises two or more hinges defining two or more corners of the frame in the open position, and altering the shape of the frame from the open shape to the closed shape comprises closing the hinges of the frame to reduce the angles defined by the corners of the frame.

These and other embodiments are described in more detail in the detailed description which follows.

BRIEF DESCRIPTION OF THE FIGURES

The invention will now be described by way of example, with reference to the accompanying figures, of which:

FIGS. 4A and 4B illustrate perspective views, and FIG. 4C illustrates a sectional view;

FIG. 5A is a plan view of a treatment area having columnar vacancies;

FIG. 5B is a plan view of a treatment area having columnar vacancies relatively larger than the columnar vacancies of FIG. 5A;

FIGS. 6A and 6B are photographs of ellipse-shaped columnar vacancies formed by fractional laser ablation;

DETAILED DESCRIPTION

Figure 1:
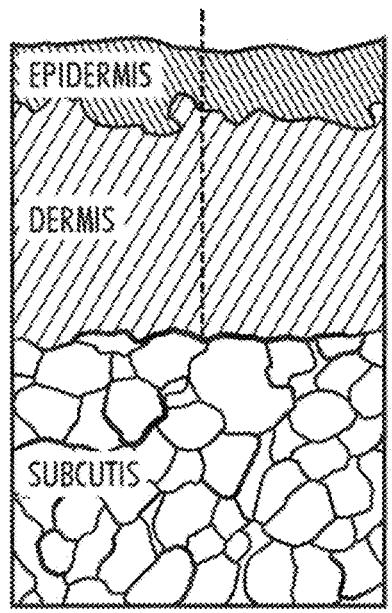
FIG. 1 is a cross-sectional view of human skin showing the epidermal, dermal, and subcutaneous layers.

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9. Similarly, a stated range of "1 to 10" should be considered to include any and all subranges beginning with a minimum value of 1 or more and ending with a maximum value of 10 or less, e.g., 1 to 5, or 4 to 10, or 3 to 7, or 5 to 8.

All ranges disclosed herein are also to be considered to include the end points of the range, unless expressly stated otherwise. For example, a range of "between 5 and 10" or "from 5 to 10" or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

I. Methods for Skin Tightening

In one aspect, methods of skin tightening are described herein, including methods of tightening the skin of a patient or subject, such as a human subject. The method can tighten the skin of a subject by removing excess skin, such as "turkey neck" or "bat wing" skin, post weight loss skin, postpartum skin, brachioplasty skin, mastopexy skin, facelift skin, neck lift skin, abdominoplasty skin, post gastric bypass surgery skin, wrinkles, or other types of excess skin. Furthermore, in some embodiments, methods of skin tightening described herein can remove scar tissue, such as surgical scars, acne scars, atrophic scars, keloid scars, hypertrophic scars, stretch marks, or other types of scars.

In one embodiment, a method for tightening skin comprises the steps of removing a column of the skin and forming a columnar vacancy in the skin, the columnar vacancy having a perimeter defined by a first side and a second side opposite the first side. The first side and the second side each comprise an epidermal layer, a dermal layer, a subcutaneous layer of skin, or any combination thereof. The method further comprises contacting and/or connecting the first side of the columnar vacancy to the second side of the columnar vacancy, thereby closing the columnar vacancy.

Figure 2A:
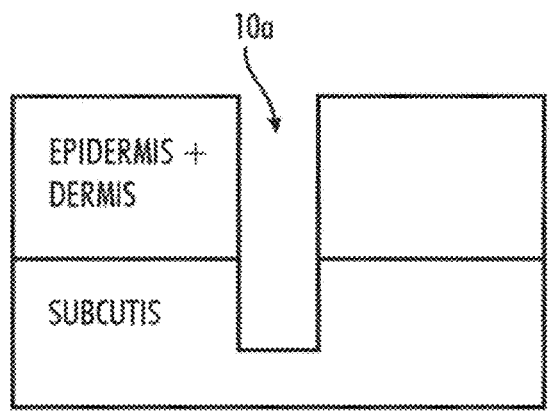
FIG. 2A is a cross-sectional view of human skin having a columnar vacancy extending through the epidermal and dermal layers into the subcutaneous layer.
Figure 2B:
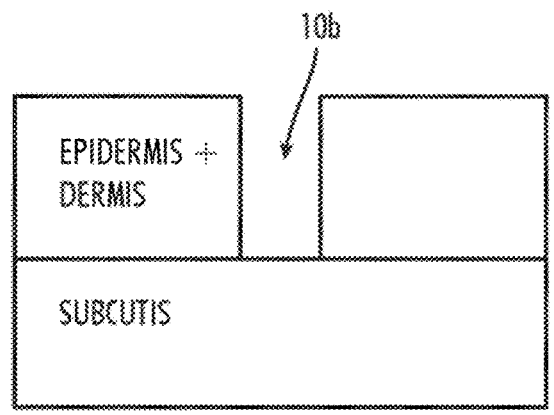
FIG. 2B is a cross-sectional view of human skin having a columnar vacancy extending through the epidermal layer into the dermal layer.

FIG. 1 shows a cross-sectional view of the various layers of human skin, with the epidermal layer being the outermost layer, the subcutaneous layer (i.e., "subcutis") being the inner most layer, and the dermal layer being a middle layer positioned between the epidermal and subcutaneous layers. The columnar vacancy is a void in which a portion of one or more of the skin layers has been removed. As seen for example in FIG. 2A, in some instances the columnar vacancy 10a can extend through the epidermal and dermal layers, into the subcutaneous layer. In other instances, as illustrated for example in FIG. 2B, the columnar vacancy 10b can extend through the epidermal layer into the dermal layer.

When the columnar vacancy is closed or connected, the epidermal layer, the dermal layer, and/or the subcutaneous layer of the first side of the columnar vacancy is aligned, respectively, with the epidermal layer, the dermal layer, and/or the subcutaneous layer of the second side of the columnar vacancy in a z-direction orthogonal to the surface of the skin. It is to be understood that such "aligned" layers, in some cases, are not offset from one another in the z-direction by more than 15%, more than 10%, or more than 5% of the thickness of the respective layers in the z-direction. In some instances, two layers that are aligned with one another are offset in the z-direction by 0-10%, 0-8%, 0-5%, or 0-3%, based on the average thickness of the two layers in the z-direction.

Additionally, in some instances, the epidermal layers, the dermal layers, and the subcutaneous layers of the first and second sides of the columnar vacancy are aligned to form a substantially planar dermal-epidermal junction and a substantially planar dermal-subcutaneous junction across the first and second sides of the columnar vacancy when the columnar vacancies are closed or connected.

Figure 3:
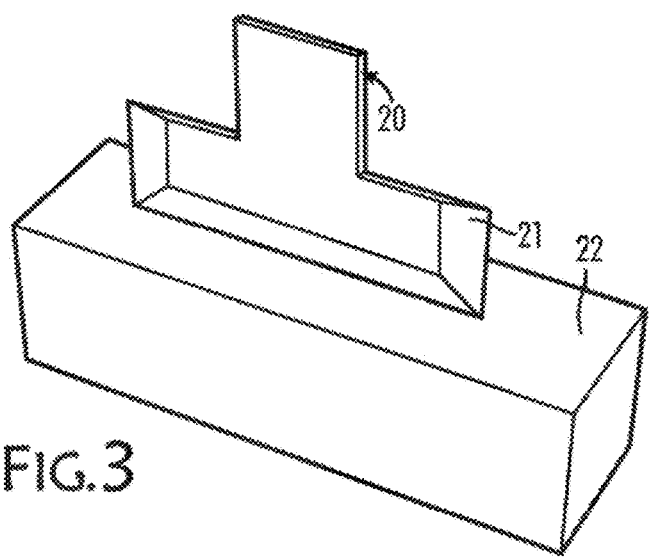
FIG. 3 is a perspective view of a mechanical excision device having a blade.

Further, in some embodiments, a method for tightening skin described herein can tighten skin on a subject using a mechanically operated excision device 20, as shown for example in FIG. 3. The excision device 20 can comprise a blade 21 that cuts a column in the skin 22 of a subject, which is removed to form a columnar void, shown for example in FIGS. 2A and 2B. For example, the excision device can comprise an oscillating blade, such as a computer controlled oscillating blade, a harmonic scalpel or equivalent device, or any other mechanically operated bladed device known to those of ordinary skill in the art not inconsistent with the objectives of this disclosure.

Moreover, in some preferred embodiments, a method for tightening skin described herein can tighten skin on a subject by using fractional laser ablation to remove one or more columns of skin. As understood by one of ordinary skill in the art, "fractional" laser ablation refers to a laser ablation process in which an ablating laser beam is used to selectively ablate, vaporize, destroy, or remove columns of tissue, or "drill holes," in a targeted area such as a treatment area of skin. In an embodiment, the step of removing a column of the skin and forming a columnar vacancy in the skin comprises performing a fractional laser ablation in a treatment area of the skin, thereby removing a column of the skin and forming a columnar vacancy in the skin. For purposes described herein, the fractional laser ablation "cuts" and removes columns of skin directly without the use of any other techniques, such as mechanical coring devices. That is, the columns of skin are removed by laser light alone. Thus, in some preferred embodiments, a method described herein does not comprise or include removing a column of skin through mechanical coring.

Figures 4A, 4B, 4C:
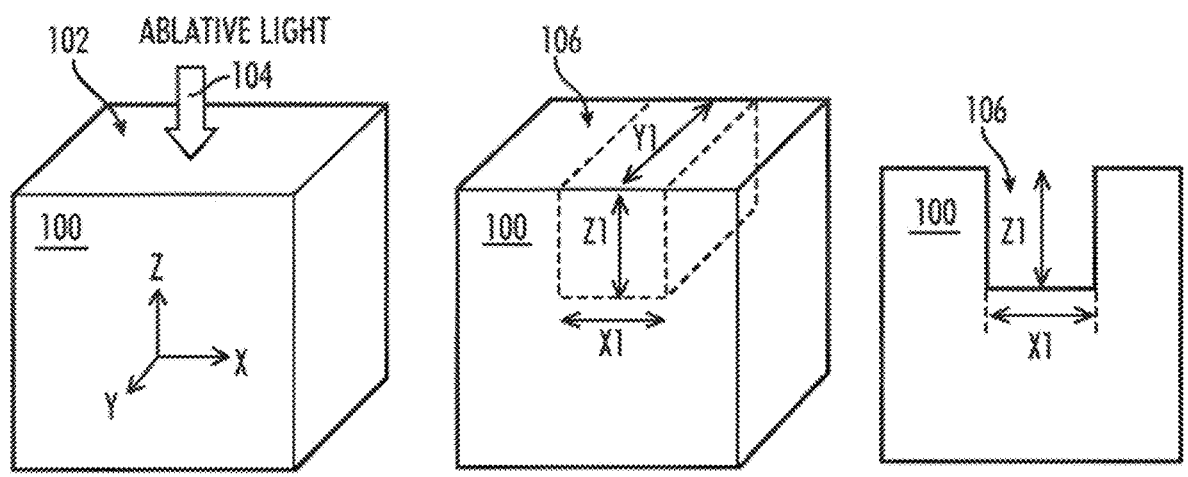
FIGS. 4A, 4B, and 4C are schematic illustrations of ablative laser treatment of skin, where

An exemplary fractional laser treatment process is illustrated in FIGS. 4A-4C, in which schematic illustrations of a subject's skin tissue 100 both during and after an ablative laser treatment are shown. As FIG. 4A illustrates, a dose of fractionally ablative laser light 104 is applied to an external surface 102 of the subject's skin during an ablative laser treatment. The laser light 104 may be orthogonally disposed relative to the surface 102 of the subject's skin or angled relative to the surface 102 of the subject's skin. The laser light 104 forms one or more circular or non-circular ablated columnar vacancies or channels 106 in the subject's skin.

It is to be understood, for reference purposes herein, that a "dose" (or "exposure") of laser light is generally not synonymous with a "pulse" of laser light, particularly not with respect to the "pulses" of laser light inherently produced by a pulsed laser (as opposed to a continuous wave laser). Instead, a "dose" of laser light in the context of the present disclosure refers to light emitted by a laser during a single, discrete "on" time of the laser, during which the laser light is directed to a treatment area described herein (or to a single spot or location within the treatment area). Moreover, the "dose" of laser light can have a duration that is greater than the pulse duration of a pulsed laser (if a pulsed laser is used). For example, in some cases, a single "dose" of laser light is at least 1 ms, at least 5 ms, at least 10 ms, at least 100 ms, at least 0.5 seconds, or at least 1 second in duration. In some cases, a "dose" of laser light described herein has a duration of 1 ms to 10 seconds, 1 ms to 5 seconds, 1 ms to 1 second, 100 ms to 10 seconds, 100 ms to 5 seconds, or 100 ms to 1 second. Moreover, a "dose" of laser light is temporally bounded on both sides by an "off" period of time during which the laser light is not directed to or incident on the treatment area (or on the single spot or location within the treatment area). Further, this "off" period of time is longer than (and different from) the time between pulses generated by a pulsed laser in continuous operation (if a pulsed laser is used).

FIGS. 4B and 4C show respective dimensional and plan views of the skin tissue 100 after application of the ablative laser light 104. In FIG. 4B, the columnar vacancy 106 is shown in broken lines for illustration purposes only, so that the x-, y-, and z-directions are readily visible. As FIGS. 4B and 4C collectively illustrate, each columnar vacancy 106 that forms during an ablative laser treatment defines a three-dimensional structure having an overall length Y1, an overall width X1, and an overall depth Z1. The overall length Y1 and/or overall width X1 of the column vacancy 106 can be symmetric or non-symmetric with respect to the z-axis in the z-direction. In some embodiments, the overall length Y1 and/or overall width X1 can vary in the z-direction in a continuous or discontinuous manner. In other embodiments, the overall length Y1 and/or overall width X1 do not vary in the z-direction. In some embodiments, the columnar vacancy is circular, polygonal, diamond-shaped, or ellipse-shaped when viewed orthogonally to the surface 102 of the skin along the z-direction.

FIGS. 6A and 6B show a pictorial view of the surface of the skin along the z-direction of a columnar vacancy formed by fractional laser ablation with a laser having a laser beam with a diamond-shaped cross-section. However, FIGS. 6A and 6B are exemplary embodiments, and the dimensions of the columnar vacancy are not limited to only those disclosed dimensions. Instead, the columnar vacancy can have any overall length, overall width, and/or overall depth not inconsistent with the objectives of this disclosure. For example, as seen in FIGS. 5A and 5B, the overall dimensions of the columnar vacancy can depend on the location of the treatment area of a subject. For example, as shown in an embodiment of FIG. 5A, the overall dimensions of the columnar vacancy 110a can be relatively small (e.g., 2 mm overall length to 1 mm overall width), such as when the location of the treatment area 111 is in a region of the body where a higher density of relatively small columnar vacancies 110a are needed. In some such instances, a columnar vacancy having a 2 mm overall length and 1 mm overall width and an ellipse shape could be used to provide 10% tissue removal by using 6.4 vacancies per square centimeter of treatment area. Similarly, a 0.5 mm×1 mm ellipse would have an area of 0.004 cm$^2$ and could provide 10% tissue removal by using 25.5 vacancies/cm$^2$. Further, when the columnar vacancy is defined by a 0.5 mm diameter circle, 10% tissue removal can be obtained using 51 vacancies/cm$^2$.

In another example, as shown in an embodiment of FIG. 5B, the overall dimensions of the columnar vacancy 110b can be relatively large (e.g. 10 mm overall length to 1 mm overall width), such as when the location of the treatment area 111 is in a region of the body where a lower density of larger columnar vacancies 110b are needed for the same sized treatment area 111. For instance, in some cases, a 10 mm×1 mm ellipse would have an area of 0.079 cm$^2$ and could provide 10% tissue removal by using 1.27 vacancies/cm$^2$.

Moreover, in some embodiments, the columnar vacancy (or, where a plurality of columnar vacancies are concerned, the average columnar vacancy) has an overall length that is 2.5 to 3.5 times greater than the overall width. In other embodiments, the ratio of overall length to overall width can be 1 to 1; 2 to 1; 3 to 1; 4 to 1; 5 to 1; 6 to 1; 7 to 1; 8 to 1; 9 to 1, 10 to 1; or >10 to 1.

The overall depth of ablation in an ablation step can vary. Any depth not inconsistent with the objectives of this disclosure may be used. For example, in some embodiments, an ablation step removes at least 90%, at least 95%, at least 98%, or at least 99% of tissue in a column of a given width to a depth of up to 1000 μm or to a depth of up to 2000 μm. In some cases, an ablation step removes at least 90%, at least 95%, at least 98%, or at least 99% of tissue in the column to a depth of 50-2000 μm, 50-1000 μm, 50-500 μm, 50-300 μm, 50-200 μm, 100-2000 μm, 100-1000 μm, 100-500 μm, 100-300 μm, 100-200 μm, 200-2000 μm, 200-1000 μm, 200-500 μm, 400-2000 μm, 400-1000 μm, 500-2000 μm, 500-1000 μm, or 1000-2000 μm.

Additionally, in some embodiments, the fractional laser ablation generates columnar vacancies having an average diameter (or average length or width) of 150-500 μm, 150-450 μm, 150-400 μm, 200-600 μm, 200-500 μm, 200-450 μm, 200-400 μm, 250-600 μm, 250-500 μm, 250-450 μm, 250-400 μm, 300-600 μm, 300-500 μm, 300-450 μm, 300-400 μm, 400-600 μm, 400-500 μm, or 450-600 μm, and a depth of 0.3-2.5 mm, 0.3-2 mm, 0.3-1.5 mm, 0.3-1 mm, 0.5-2.5 mm, 0.5-2 mm, 0.5-1.5 mm, 0.5-1 mm, 1-2.5 mm, or 1-2 mm.

It is to be understood that a "laser" can refer to a single lasing device that produces a single beam of laser light from a single lasing medium. The laser described herein can be a pulsed laser or a continuous wave (CW) laser. Moreover, when a pulsed laser is used, the laser can produce time-modulated pulses of the laser beam. For instance, in some cases, the laser beam comprises an ablative laser beam and the laser produces time-modulated pulses of the ablative laser beam.

A laser or laser beam described herein can have any power and any peak or average emission wavelength not inconsistent with the objectives of this disclosure. For example, in some embodiments, a laser or laser beam of a device described herein has a peak or average emission wavelength in the infrared (IR) region of the electromagnetic spectrum. In some such cases, the laser or laser beam has a peak or average emission wavelength in the range of 1-4 µm, 1-3 µm, 2-4 µm, 2-3 µm, 8-12 µm, or 9-11 µm. For example, in some embodiments, the laser or laser beam comprises an erbium-doped yttrium aluminum garnet (Er:YAG) laser or laser beam or a neodymium-doped YAG (Nd:YAG) laser or laser beam having a peak or average emission wavelength of 2940 nm or 1064 nm. In other cases, the laser or laser beam comprises a carbon dioxide laser or laser beam. A laser beam described herein can also have a peak or average emission wavelength in the visible region of the electromagnetic spectrum. Non-limiting examples of peak or average emission wavelengths suitable for use in some embodiments described herein include 532 nm, 695 nm, 755 nm, 1064 nm, and 1470 nm (e.g., for non-ablative application), or 2940 nm (e.g., for ablative application). Further, in some instances, a laser or laser beam of a device described herein has an average power of 1 to 10 W (e.g., when used for non-ablation) or 50 to 200 W (e.g., when used for ablation).

Moreover, the spot size of a laser beam produced by a laser described herein may also vary. Any spot size not inconsistent with the objectives of the disclosure may be used. In some cases, for instance, the spot size is 0.1-10 mm, 0.1-1 mm, 0.1-0.5 mm, 0.5-5 mm, 1-10 mm, or 1-5 mm. Other spot sizes may also be used.

Figure 7:
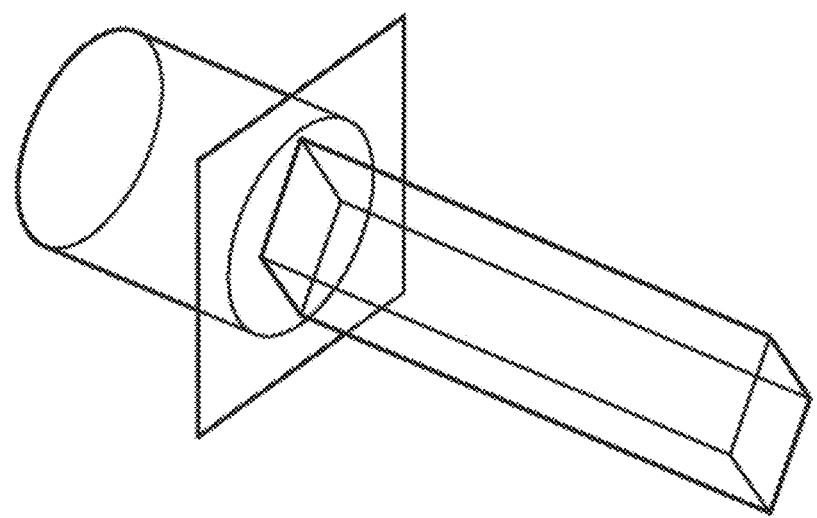
FIG. 7 is a perspective view of a schematic illustration of laser beam having a diamond-shaped cross-section.
Figure 8:
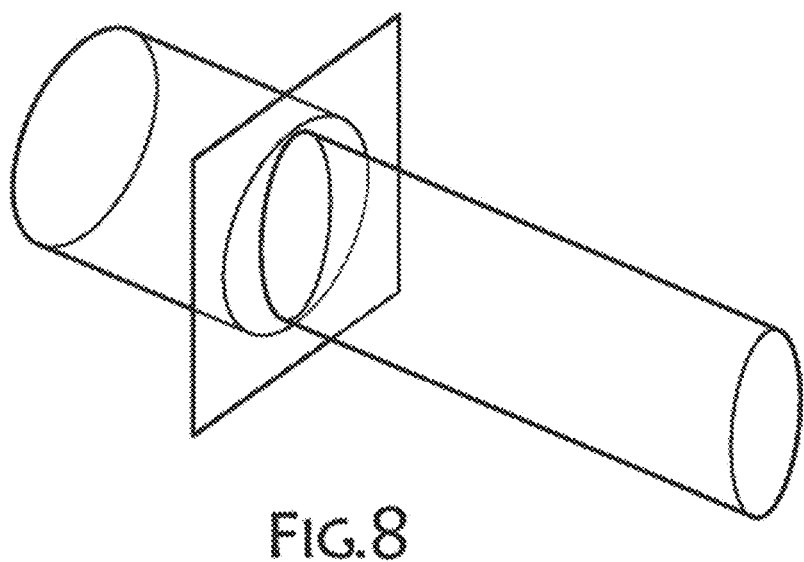
FIG. 8 is a perspective view of a schematic illustration of a laser beam having an ellipse-shaped cross-section.

As described above, the laser beam can have any cross-sectional shape not inconsistent with the objectives of this disclosure. For example, in some instances, the laser beam has a circular, polygonal, diamond-shaped, or ellipse-shaped cross-section. In the instance shown in FIG. 7, a laser beam having a diamond-shaped cross-section is described, and in the instance shown in FIG. 8, a laser beam having an ellipse-shaped cross-section is described.

Figure 9A:
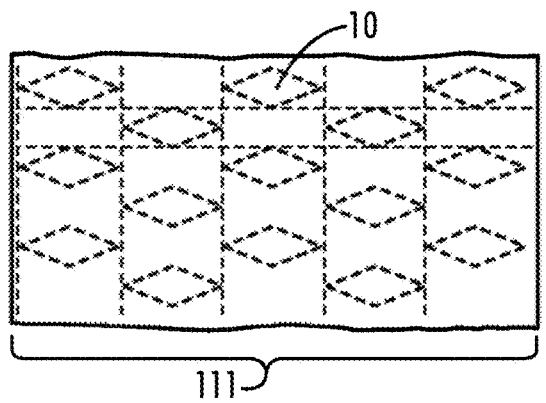
FIGS. 9A and 9B are plan views of a plurality of columnar vacancies in a treatment area having different cutting patterns.
Figure 9B:
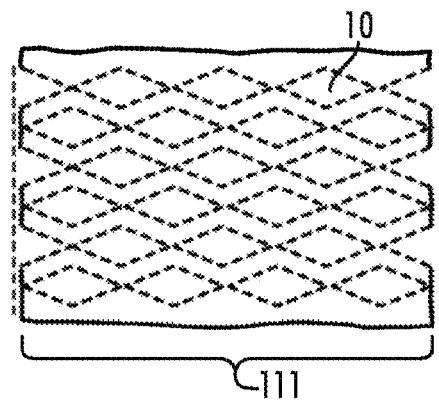

In some embodiments, the method of skin tightening further comprises removing a plurality of columns of skin (as opposed to only a single column of skin) from a treatment area using fractional laser ablation, and forming a plurality of columnar vacancies (as opposed to a single vacancy) in the treatment area. The dimensions of each individual column of skin removed can be substantially equal to each other in some instances, such as is shown in FIGS. 9A and 9B. In other instances, the dimensions of the each individual column of skin removed can be different from each other. Moreover, each columnar vacancy, or any given columnar vacancy, can have a size and/or shape described hereinabove for a single columnar vacancy.

The plurality of columns can be removed from the treatment area in any pattern not inconsistent with the objectives of this disclosure. In the embodiments shown in FIGS. 9A and 9B, a grid-like pattern of columns and rows can be formed by the columnar vacancies 10 within the treatment area 111. In some instances, the columnar vacancies 10 in adjacent columns are staggered such that the columnar vacancies 10 in adjacent columns are in different rows, and columnar vacancies 10 in every other column are in the same rows. In an embodiment shown in FIG. 9A, the columnar vacancies 10 in adjacent columns can be positioned within their respective columns without substantially overlapping into their respective adjacent column, and every other row within a column. In the embodiment shown in FIG. 9B, the columnar vacancies 10 in every other row overlap into the adjacent column. Thus, depending on the particular location of the treatment area 111 on a subject and desired levels of skin tightening, the density of the plurality of columnar vacancies in the treatment area 111 can be relatively low (e.g., FIG. 9A) or relatively high (e.g., FIG. 9B). Moreover, in the instance shown in FIG. 5B, the columnar vacancies 10 within a treatment area can comprise a single column, or, in other embodiments (not shown), a single row within a treatment area, where the number of columnar vacancies within the treatment area are relatively low compared to the patterns in FIGS. 9A and 9B, with each columnar vacancy being relatively large.

The treatment area can be any size not inconsistent with the goals of this disclosure. For example, the treatment area can have an area of 10 mm 2 to 1,000 cm²; 20 mm 2 to 1,000 cm²; 30 mm 2 to 1,000 cm²; 40 mm 2 to 1,000 cm²; 40 mm 2 to 1,000 cm²; 50 mm 2 to 1,000 cm²; 60 mm 2 to 1,000 cm²; 70 mm 2 to 1,000 cm²; 80 mm 2 to 1,000 cm²; 90 mm 2 to 1,000 cm²; 100 mm 2 to 1,000 cm²; 200 mm 2 to 1,000 cm²; 300 mm 2 to 1,000 cm²; 400 mm 2 to 1,000 cm²; 500 mm 2 to 1,000 cm²; 600 mm 2 to 1,000 cm²; 700 mm 2 to 1,000 cm²; 800 mm 2 to 1,000 cm²; 900 mm 2 to 1,000 cm²; or 1 cm² to 1,000 cm².

In an embodiment, the method of skin tightening further comprises imaging blood vessels in the treatment area prior to performing the fractional laser ablation, thereby forming a map of the vascularized and non-vascularized regions in the treatment area. Such imaging can be carried out with any imaging system not inconsistent with the objectives of the present disclosure. For example, in some cases, the imaging system can comprise an optical imaging system, such as an optical coherence tomography (OCT) system, a multi-photon imaging system, a reflectance confocal microscopy (RCM) system or any other imaging system not inconsistent with the objectives of this disclosure. In some instances, a selectively reflective optical element can be configured to reflect both an outgoing beam and a return signal of the optical imaging system to permit the imaging system to both "probe" a target area and also receive a return signal from the target area. For instance, in the case of an OCT imaging system, the imaging system can comprise an OCT pilot or probing beam generator and an OCT detector.

In other embodiments, the imaging system of a system or method described herein comprises an acoustic imaging system. For instance, in some cases, the imaging system is an ultrasound imaging system. Such a system can comprise one or more ultrasound transducers and/or receivers as commonly known in the art.

The use of these imaging systems is beneficial when imaging beneath the surface of skin is needed or desired, such as to non-invasively image a structure of skin or blood vessels beneath the surface. An OCT or other imaging system described herein can be used to image a component or structure of skin (such as a blood vessel) at any depth not inconsistent with the objectives of this disclosure. For example, in some cases, a blood vessel is imaged by the imaging system at a depth of up to 2 mm, up to 1 mm, or up to 0.5 mm.

As described above, in some embodiments, the imaging systems images blood vessels in the treatment area of the skin, and creates a map of vascularized and non-vascularized regions of the treatment area. It is to be understood that a "vascularized" region is a region or volume of tissue including vessels, particularly blood vessels. Similarly, a "non-vascularized" region is a region or volume of tissue that does not include blood vessels. Using the map generated by the imaging system, the pattern of columns to be removed by fractional laser ablation of the treatment area can be determined based on the location of blood vessels. For example, in some instances, the fractional laser ablation is performed substantially on the non-vascularized regions of the treatment area, such that vascularized tissue is not ablated. When fractional laser ablation is performed "substantially" on non-vascularized regions (as opposed to vascularized regions), the tissue that is ablated, vaporized, destroyed, or removed by the fractional laser ablation can be at least 50%, at least 60%, at least 70%, at least 80%, at least 85%, at least 90%, at least 95%, at least 98%, or at least 99% non-vascularized tissue (as opposed to vascularized tissue). By targeting the non-vascularized regions/tissue, bleeding from the columnar vacancies can be reduced or minimized in the treatment area. Additionally, the rate of wound healing can be increased, and the amount of bruising can be decreased.

Further, in some cases, a method of tightening skin and/or reducing scar tissue comprises a step of automatedly controlling the fractional laser ablation and imaging of blood vessels. For example, computer hardware and/or software can be operatively connected to the laser and the imaging system, and can carry out or control the imaging and/or ablation steps described herein. As shown for example in FIG. 10, a computer or controller 200 can include a processor 205 and a non-transitory memory 210 storing computer-readable program code that, in response to execution by the processor 205, cause instructions to be provided to a laser 215, an imaging system 220, or both in a desired sequence. Any hardware and/or software not inconsistent with the objectives of the disclosure may be incorporated into or used with the computer or controller 200 described herein. Moreover, various suitable hardware and software components will be readily apparent to those of ordinary skill in the art. Such hardware and/or software can also be used to carry out any step or computational task not inconsistent with the objectives of the disclosure.

Figure 11:
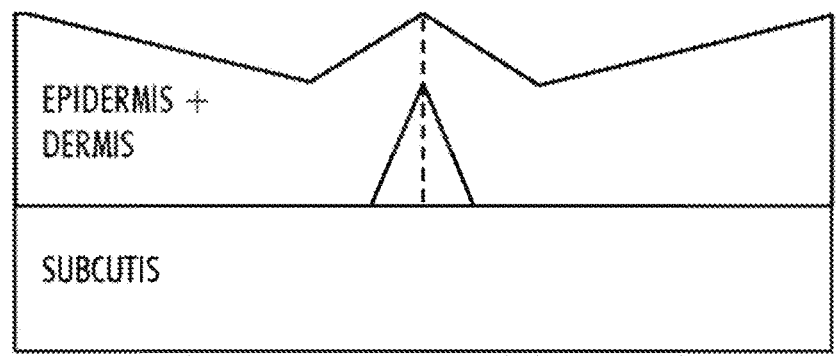
FIG. 11 schematically illustrates a sectional view of skin having a columnar vacancy that extends through the epidermal and dermal layers, where the epidermal and dermal layers are brought together to close the columnar vacancy.
Figure 12:
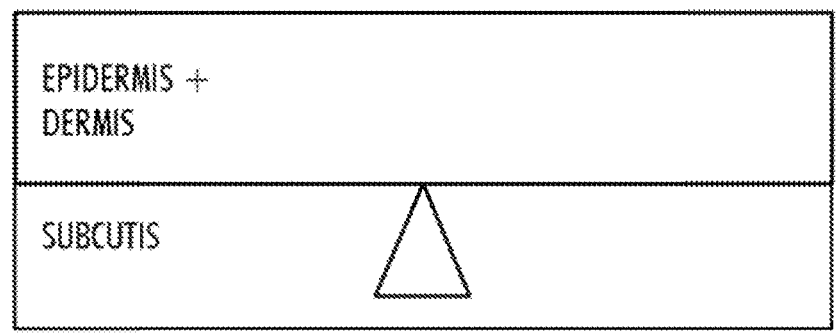
FIG. 12 schematically illustrates a sectional view of skin having a columnar vacancy that extends through the epidermal and dermal layers into the subcutaneous layer, where all three layers are brought together to close the columnar vacancy.

As described above, a columnar vacancy can be closed by contacting or connecting the first side of the columnar vacancy to the second side of the columnar vacancy. Stated differently, the columnar vacancy can be closed by bringing together one or more of the epidermal, dermal, and subcutaneous layers. For example, when the columnar void extends through the epidermal and dermal layers, but not the subcutaneous layer, the epidermal and dermal layers can be brought together, such as is shown in FIG. 11. In instances where the columnar vacancy extends into the subcutaneous layer, such as is shown in FIG. 12, all three layers can be brought together. In some preferred embodiments, the alignment and closing illustrated in FIG. 12 is achieved.

The first and second sides of the columnar vacancy can be brought together in any manner not inconsistent with the objectives of the present disclosure. For instance, in some cases, the first and second sides are brought together manually by squeezing or compressing the skin on the first and second sides together using one's fingers. The first and second sides can alternatively be brought together using mechanical devices to close the columnar vacancy, such as are described in more detail below.

Figure 13A:
FIG. 13A is a photograph of an open columnar vacancy in skin.
Figure 13B:
FIG. 13B is a photograph of the columnar vacancy of FIG. 13A being manually closed and an adhesive being applied over the closed columnar vacancy.
Figure 13C:
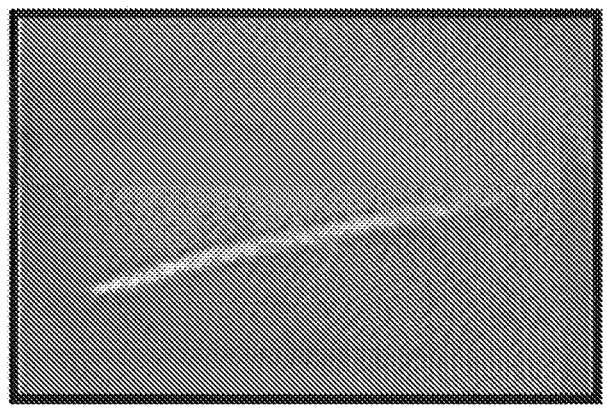
FIG. 13C is a photograph of the closed columnar vacancy of FIG. 13B being held closed by the applied adhesive.
Figure 14:
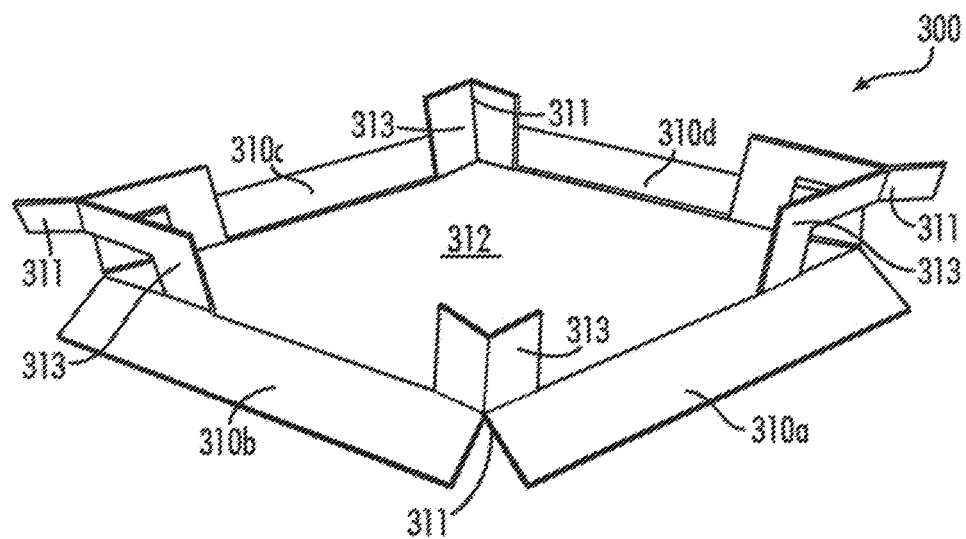
FIG. 14 is a perspective view of a side of a frame in an open position.
Figure 15:
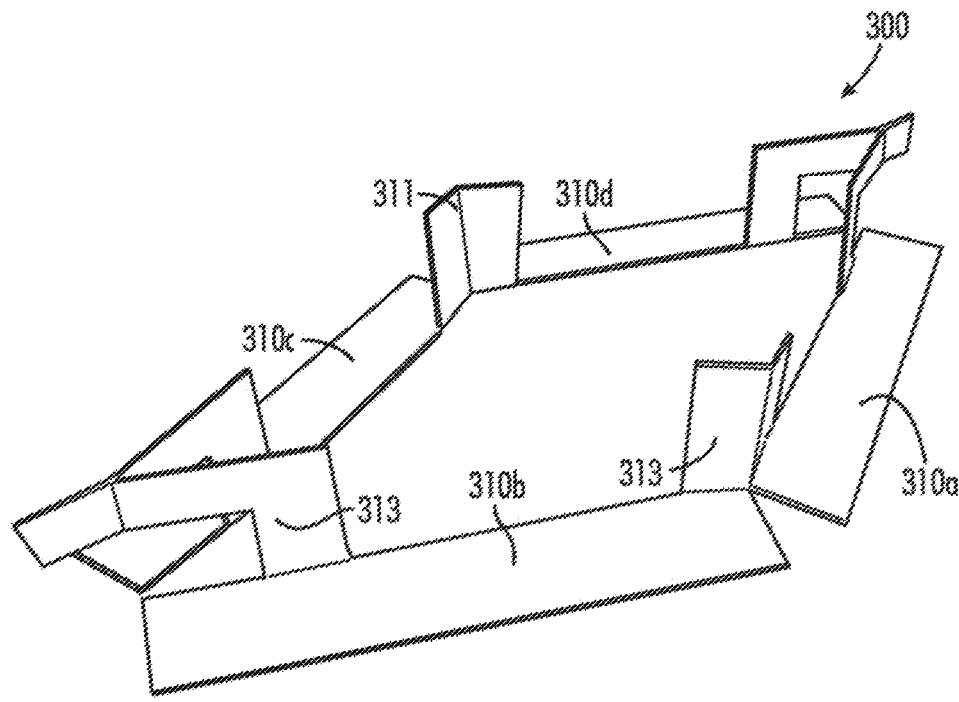
FIG. 15 is a perspective view of a frame in an open position.
Figure 16:
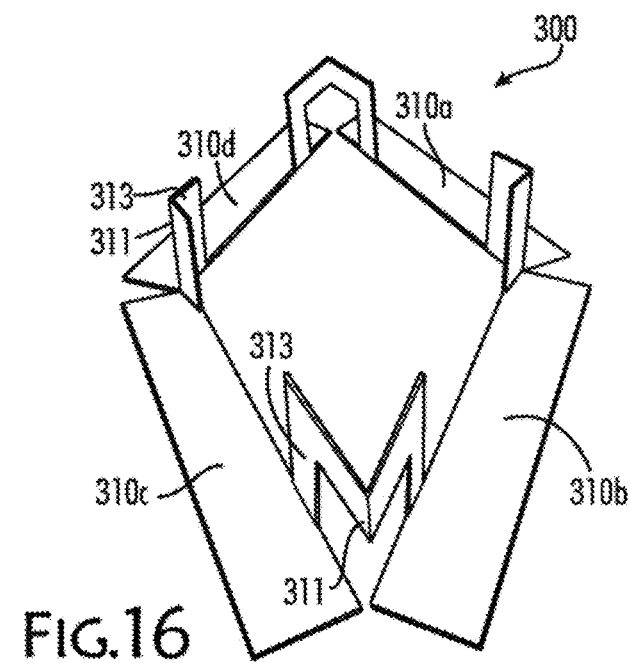
FIG. 16 is a perspective view of an end of a frame in an open position.
Figure 17:
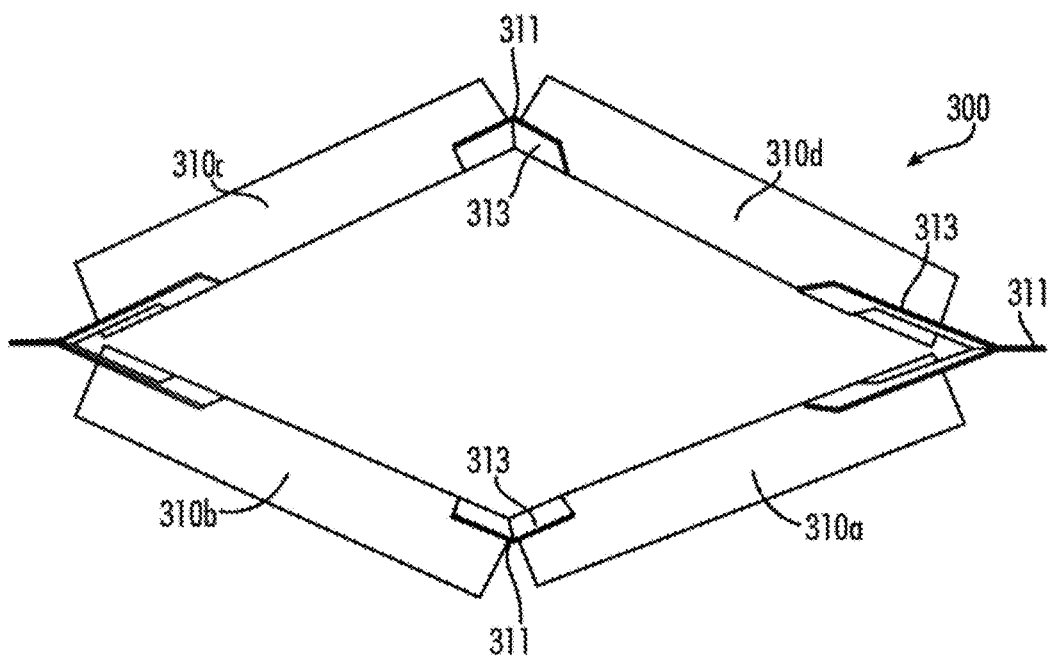
FIG. 17 is a plan view of a frame in an open position.
Figure 18:
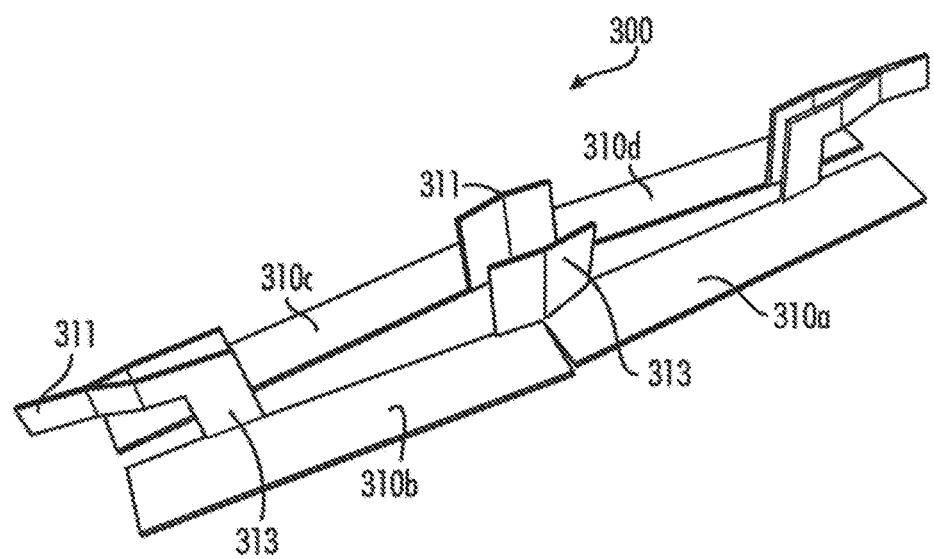
FIG. 18 is a perspective view of a frame in a closed position.

When the columnar vacancy is closed manually (or otherwise, but particularly manually), the method of skin tightening described herein can further comprise applying an adhesive to the skin of a subject over the closed columnar vacancy. For example, FIG. 13a shows an exemplary columnar vacancy that is "open". The columnar vacancy is shown as being manually closed and an adhesive being applied to the closed columnar vacancy in FIG. 13b, and FIG. 13c shows the closed columnar vacancy being held in the "closed" position by the adhesive. The adhesive can be any biologically compatible adhesive known to those of ordinary skill in the art that is not inconsistent with the objectives of this disclosure. For example, in some instances the adhesive can be a urethane polymer-based adhesive, such as the commercial product TEGADERM® (available from 3M). When a compressive adhesive dressing such as TEGADERM® is used, different sizes and shapes can be fashioned to facilitate placement on various regions of the body. The compressive adhesive dressing can be manually stretched prior to application on the skin over the columnar vacancy, or can be pre-stretched using an applicator device. The pre-stretched compressive adhesive dressing can then be positioned over the columnar vacancy and adhered to the skin. The compressive adhesive dressing can then be allowed to relax (e.g., through contraction), thus applying a compressive force to the closed columnar vacancy, allowing the columnar vacancy to remain closed during the healing process. In other instances, the adhesive can be a cyanoacrylate polymer-based adhesive, such as the commercial product DERMABOND® (available from Ethicon). Other adhesives may also be used, including either naturally occurring or synthetic polymers. In some cases, an adhesive is a bioadhesive or a biomimicry adhesive, such as a gelatin or L-DOPA adhesive. Exemplary adhesives that may be used in a method described herein include polyphenolic protein adhesives and polysaccharides. When such adhesives are used, again with reference to FIGS. 13a-13c, the skin can be manually compressed together to close the columnar vacancy, and the adhesive applied to the skin, thus maintaining the compressed state of the skin.

Figure 23:
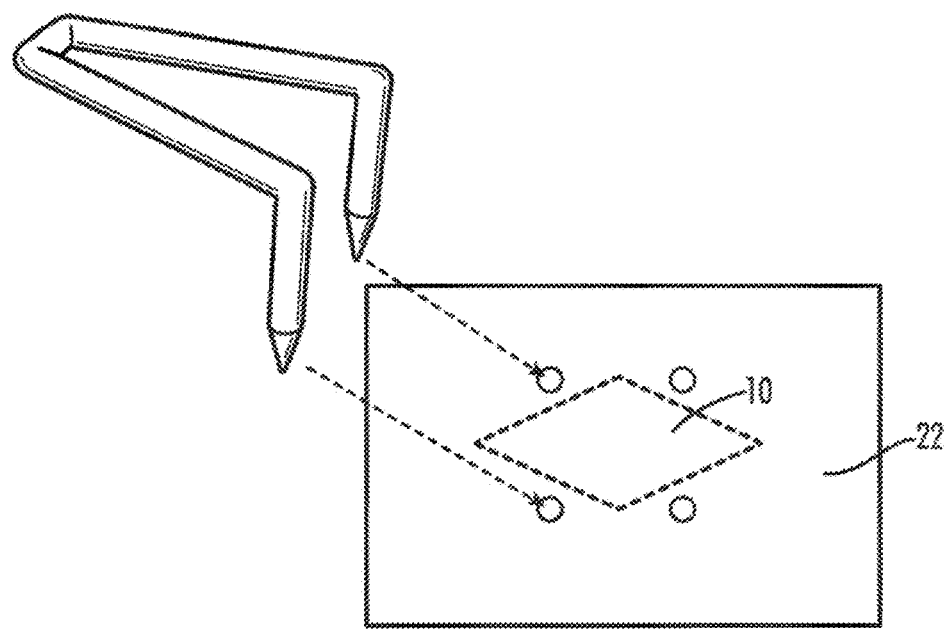
FIG. 23 is a perspective view of a staple used to hold a columnar vacancy closed.

Moreover, in some embodiments, absorbable sutures or staples can be used to assist the adhesive in holding the columnar vacancy closed. For example, as shown in FIG. 23, absorbable fish barb sutures/staples can be inserted into the skin to provide mechanical support to the chemical bonding of the adhesive. The absorbable sutures can be inserted at any therapeutically useful depth, such as 0.5 mm, 1 mm, 1.5 mm, or 2 mm.

Moreover, the adhesive can be transparent to light or substantially transparent to light. More particularly, in some preferred embodiments, the adhesive is transparent or substantially transparent to light having a wavelength that can be used to non-ablatively irradiate a closed columnar vacancy underlying the adhesive. When the adhesive is transparent to light, a method of tightening skin described herein can further comprise the step of irradiating the closed columnar vacancy with a non-ablative laser or broad band light ("BBL") beam or source through the applied adhesive. In some such cases, the adhesive is transparent or optically transparent in the infrared region of the electromagnetic spectrum or the visible region of the spectrum or in some other region of the spectrum corresponding to or overlapping with the peak wavelength or average wavelength of, respectively, the non-ablative laser beam or BBL beam. For example, in some instances, the adhesive has an optical transparency of at least 40%, at least 50%, at least 60%, at least 70%, at least 80%, at least 85%, at least 90%, or at least 95% in a desired region of the spectrum, where the transparency is based on percent transmission of incident light within the desired region. As stated above, the desired region generally includes the peak wavelength or average wavelength of the non-ablative laser light or BBL. In some exemplary embodiments, the adhesive has a transparency recited above (e.g., at least 60% transmission) within one or more of the following spectral windows: 350-750 nm, 450-750 nm, 450-700 nm, 500-750 nm, 500-700 nm, 550-750 nm, 600-750 nm, 800-1400 nm, 800-1200 nm, and 800-1100 nm. The step of irradiating the closed columnar vacancy as described herein, in some cases, can have a therapeutic effect on the columnar vacancy and/or provide one or more therapeutically beneficial effects to the subject. For example, the step of irradiating can cause or contribute to hemostasis, coagulation, or both of the closed columnar vacancy. In other instances, the step of irradiating triggers a "heat shock" response in and/or around the closed columnar vacancy wound, triggering the body to produce a variety of heat shock proteins ("HSP") that reduce inflammation and scarring, and accelerate wound healing time. In addition, the accelerated wound healing achieved by a method described herein can permit bandages or other dressings applied to the treatment area (e.g., on the face) of the patient to be removed after a shorter period of time than otherwise possible. Compressive bandages or dressings in particular can be removed after a shorter period of time.

As understood by one of ordinary skill in the art, the terms "BBL" source and "BBL beam" can refer to a source and beam, respectively, of intense, broad-spectrum pulses of light, including as defined and approved by the U.S. Food and Drug Administration. More particularly, a BBL beam produced by a BBL source can comprise pulses of non-coherent or non-laser light having a wavelength from 500 nm to 1200 nm, as described, for instance, in Raulin et al., "IPL technology: a review," Lasers Surg. Med. 2003, 32:78-87. Any laser, BBL source, laser beam, or BBL beam not inconsistent with the objectives of this disclosure can be used. Moreover, the choice of laser, BBL source, or laser or BBL beam can be based on a desired effect of the laser or BBL beam and/or on a desired target of the laser or BBL beam, such as a specific adhesive and/or columnar vacancy. A BBL source described herein generally produces a pulsed light output. In some cases, the BBL source comprises a xenon gas-filled chamber. In such instances, the BBL source can produce a BBL beam by the application of bursts or pulses of electrical current through the xenon-containing chamber.

As stated above, the irradiating beam is substantially non-ablative, and is therefore used for different purposes than the ablative fractional laser beam previously described herein that removes columns of skin. In this embodiment, the non-ablative irradiating beam can be coagulative, where a "coagulative" beam is understood to cause coagulation of tissue in and/or around the closed columnar vacancy. In another embodiment, the non-ablative irradiating beam can be hemostatic, where a "hemostatic" beam is understood to slow, reduce, or stop bleeding from the closed columnar vacancy.

Further, in some embodiments, the laser previously described herein can comprise a hybrid laser operable to produce laser beams having a plurality of differing wavelengths. For instance, in some cases, the hybrid laser is operable to selectively produce an ablative laser beam and a non-ablative laser beam. It is also possible to use both a BBL source and a laser integrated into the same device. Thus, in some embodiments, a single device described herein can be used to produce and deliver one or more beams (e.g., one or more laser beams, or one or more laser beams in combination with a BBL beam) having a range of properties, as needed for a specific treatment or other application of the device.

In another aspect, a method 400 of skin tightening uses a mechanical device to close the columnar vacancy and connect the first side of the columnar vacancy to the opposing second side of the columnar vacancy. Unless expressly stated otherwise below, the method 400 optionally comprises the steps and elements previously discussed herein, such as imaging blood vessels in the treatment area prior to removal of the columns of skin, the use of a mechanical excision device or ablative fractional laser to remove the columns of skin, and other such steps and elements.

Figure 21:
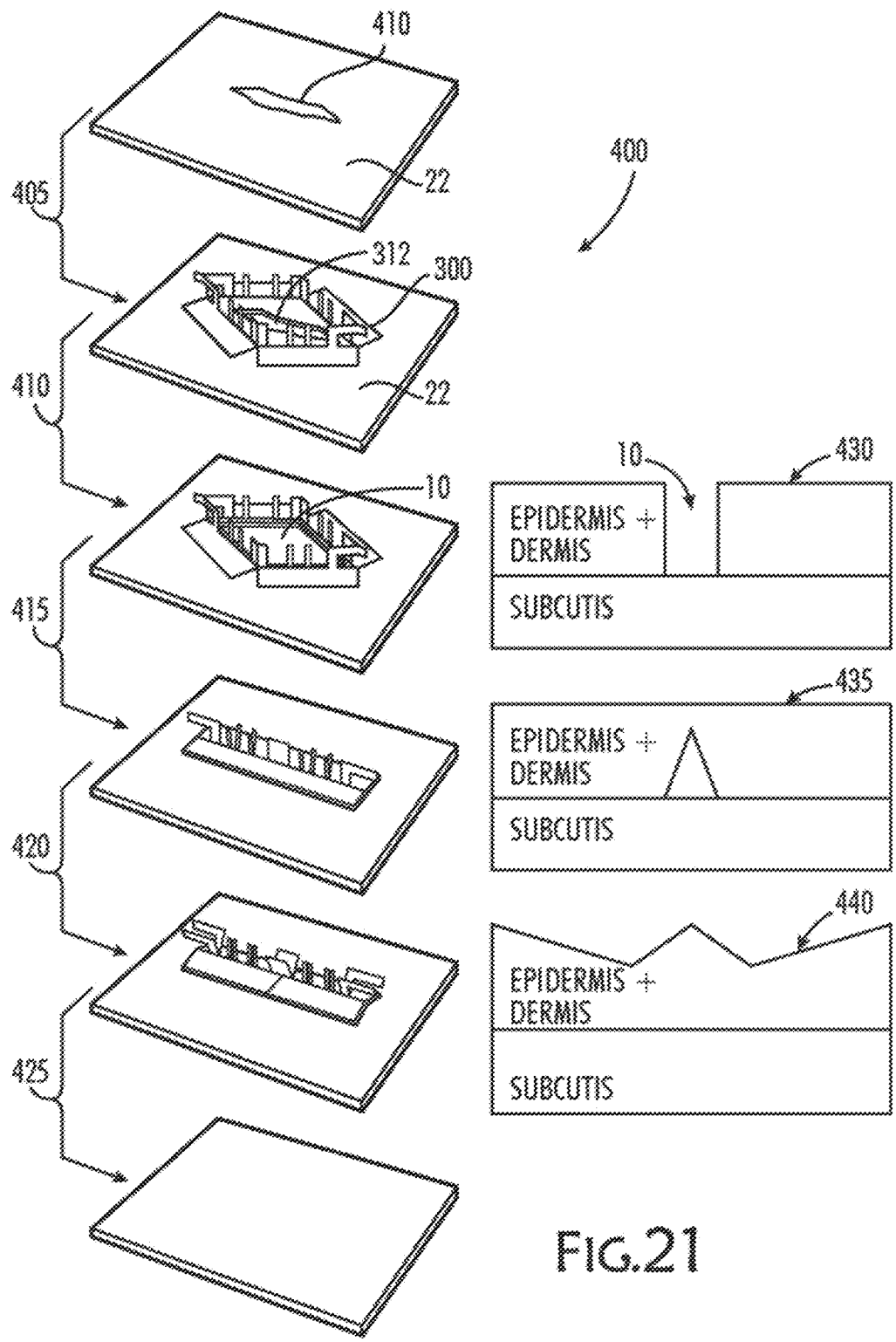
FIG. 21 illustrates steps of a method of tightening skin using a frame of FIGS. 14-20.

In an embodiment shown in FIG. 21, the method 400 comprises attaching a frame 300, in an open position, to the surface of the skin 22, wherein the frame 300 surrounds a treatment area or portion of the treatment area of the skin at step 405 (as illustrated in FIG. 21, the treatment area includes a scar or wound 401); removing a column of skin from within an interior area 312 of the frame by ablating the skin with a laser or mechanically removing the column of skin with the excision device 20, thereby forming the previously discussed columnar vacancy 10 in the skin at step 410; altering the shape of the frame 300 while the frame 300 is attached to the surface of the skin 22 from an open shape of the open position of the frame 300 to a closed shape of a closed position of the frame at step 415, wherein altering the shape of the frame 300 from the open shape to the closed shape connects the first side of the columnar vacancies to the second side of the columnar vacancy, as shown for example in reference numbers 430-440. Reference numbers 430-440 particularly show the corresponding creation of the columnar vacancy (reference number 430), the initial closing of the columnar vacancy (reference number 435), and the healed columnar vacancy (reference number 440). When the frame 300 is in a closed position, the epidermal layer, the dermal layer, and/or the subcutaneous layer of the first side of the columnar vacancy is aligned, respectively, with the epidermal layer, the dermal layer, and/or the subcutaneous layer of the second side of the columnar vacancy in a z-direction orthogonal to the surface of the skin (e.g., as shown in reference numbers 430-440).

When the frame 300 is positioned on the skin in the closed position, the epidermal layers, the dermal layers, and/or the subcutaneous layers of the first and second sides of the columnar vacancy are substantially relaxed or untensioned, allowing the closed columnar vacancy to heal in the absence or substantial absence of mechanical tension. Moreover, when the frame 300 is in the closed position, the epidermal layers, the dermal layers, and the subcutaneous layers of the first and second sides of the columnar vacancy are aligned to form a substantially planar and untensioned dermal-epidermal junction and a substantially planar and untensioned dermal-subcutaneous junction across the first and second sides of the columnar vacancy, In an embodiment, the method of skin tightening further comprises retaining the frame 300 in the closed position on the surface of the skin 22 during healing of the closed columnar vacancy at step 420 (e.g., reference number 435), and removing the frame from the surface of the skin following healing of the closed columnar vacancy at step 425 (e.g., reference number 440).

The frame 300 can be made from any biologically compatible material not inconsistent with the objectives of this disclosure. For example, the frame 300 can be made from a metal, a plastic, or a composite material.

FIGS. 14-18 show an exemplary embodiment of a frame 300. In an embodiment, the frame 300 comprises two or more rigid members 310a-310d connected together by a plurality of hinges 311. In some instances, the rigid members 310a-310d are connected together by two or more hinges 311 defining two or more corners of the frame 300 in an open position. In other instances, the rigid members 310a-310d are connected together by four or more hinges 311 defining four or more corners of the frame 300 in the open position. In the embodiments shown in FIGS. 14-17, the frame 300 is in the open position forming an internal area 312 defined by four rigid members 310a-310b and four hinges 311 connecting the four rigid members 310a-310b. In the open position, the frame 300 can have a polygonal shape as defined by edges of the four rigid members 310a-310b, such as a diamond shape. While FIGS. 14-18 show four rigid members 310a-310b, the frame 300 can comprise a plurality of rigid members connected by a corresponding number of hinges. In instances where five or more rigid members comprise the frame 300, the open shape of the fame can form different shapes, such as a hexagonal shape or other shapes.

A plurality of tabs 313 are connected to the rigid members 310a-310b. In some embodiments, the tabs 313 extend orthogonally from edges of the rigid members 310a-310b. The tabs 313 can in some embodiments form the hinges 311, such as shown in FIGS. 14-18. Particularly for the embodiment of FIGS. 14-18, four tabs 313 together form two opposing middle hinges 311a and two opposing end hinges 311b.

The shape of the frame 300 can be altered from the open position to the closed position by closing, opening, or closing and opening a combination of the hinges 311. As shown for example in FIG. 18 where the frame 300 is in a closed position, a position of two of the rigid members 310a, 310b on a first side of the frame 300 have been moved toward a position of the two opposite rigid members 310c, 310d. Correspondingly for the closed position, the angles of the two middle hinges 311a have been increased, whereas the angles of the two second end hinges 311b have been decreased as compared to FIGS. 14-18 where the frame 300 is in the open position. When the frame 300 is in the closed position, the frame 300 has a closed shape that is generally arcuate or linear, and the internal area 312 has been substantially reduced in size. Furthermore, when in the closed position, the frame 300 resists distorting substantially in the z-direction by the tabs 313.

In some embodiments, the frame 300 can be manually closed by squeezing two or more of the tabs 313 together using one's fingers. In other instances, an external apparatus (not shown) can be used to alter the shape of the frame 300 from the open position to the closed position. The external apparatus can be a clip-like apparatus that grasps and pulls two or more tabs 313 together. The external apparatus can be removed after performing the closing operation, or can be remain connected to the frame 300, serving to fix and hold the frame 300 in the closed position. In another embodiment, after the frame 300 has been closed, the tabs 313 can be bent together to lock the frame 300 in the closed position. In some instances, use of the external apparatus to alter the shape of the frame 300 from the open position to the closed position prevents the frame from distorting substantially in the z-direction. In yet another embodiment, the frame 300 can be held in the closed position by applying an adhesive over the frame 300, such as one of the adhesives previously discussed herein or any other adhesive not inconsistent with the goals of this disclosure.

Figure 19A:
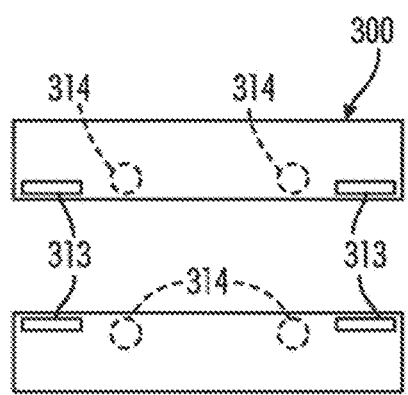
FIG. 19A is a plan view of two opposing rigid members with tabs and staples.
Figure 19B:
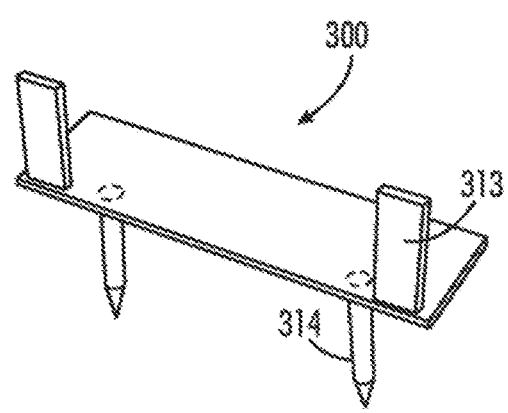
FIG. 19B is a perspective view of a rigid member with tabs and staples.
Figure 20:
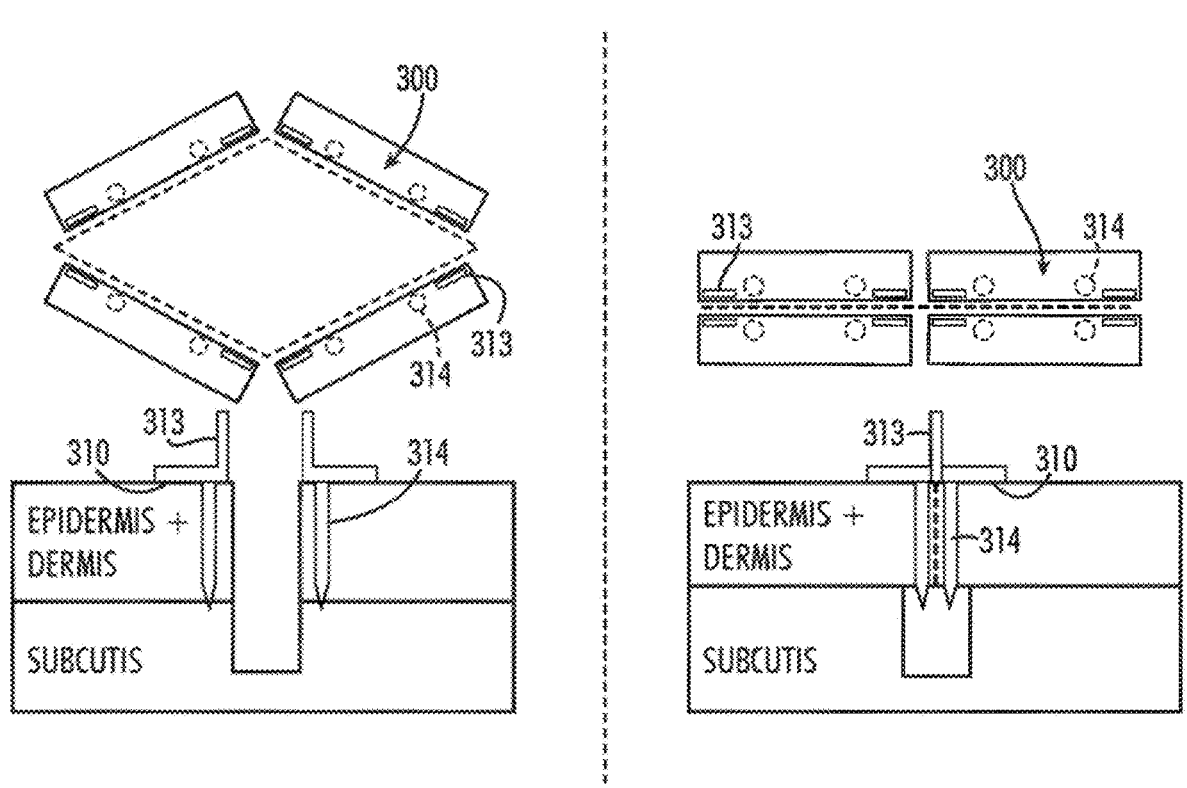
FIG. 20 is an illustration of columnar vacancies being closed using a frame having tabs and staples.

The frame 300 can be attached to the surface of the skin in the open position by a variety of mechanisms. For example, the rigid members 310a-310b can be glued or adhered to the skin surface using an adhesive, such as one of the adhesives previously discussed herein. In other embodiments, such as those shown in FIGS. 19a and 19b, the rigid members 310a-310b can comprise one or more downwardly extending staples, pins, or anchors 314 that can be inserted into the skin. The length of the staples 314 can vary based on a depth of the columnar vacancy. For example, the length of the staples 314 can be substantially equal to a depth of the columnar vacancy, such that the staples 314 push/pull the full depth of the skin together to contact and connect the first side to the second side of the columnar vacancy. In other instances, such as the embodiment shown in FIG. 20, the length of the staples 314 can be less than the full depth of the columnar vacancy.

Figure 22:
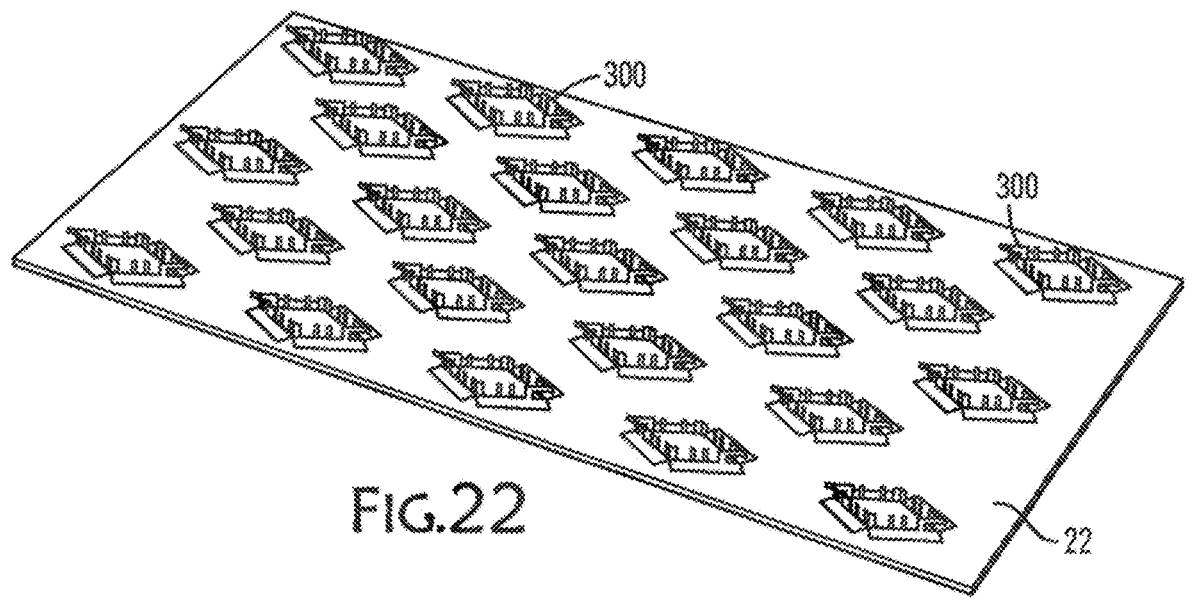
FIG. 22 is a perspective view of a plurality of the frames from any of FIGS. 14-20 positioned on a skin surface.

The method 400 can further comprise attaching a plurality of frames 300, each in an open position, to the surface of the skin 22 within a treatment area, as shown for example in FIG. 22. As previously described herein, the method 400 can comprise removing the columns of skin from the interior area 312 of each of the frames 300 using a mechanical excision device or a fractional ablative laser to form a plurality of columnar vacancies, each columnar vacancy being in the interior area 312 of a frame 300. The plurality of frames 300 can be positioned within the treatment are based on the blood vessel mapping performed using the imaging system, such that the interior areas 312 of the frames 300 are positioned over substantially non-vascularized areas of the skin.

Each frame 300 can be altered or actuated from the open position to the closed position manually, by using an external apparatus previously described herein, or using a prestretched adhesive such as TEGADERM®. The alteration or actuation of the frames 300 can be performed one at a time, or multiple frames 300 at once. The prestretched TEGADERM® can be applied over the plurality of open frames 300 to compressively close the frames 300 as the prestreched adhesive relaxes upon application or can be applied over the plurality of closed frames 300 to hold the frames 300 in the closed position. In other instances an adhesive such DERMABOND® can be applied over the closed frames 300 to hold the frames 300 in the closed position. Moreover, the tabs 313 can be bent together to lock each of the frames 300 in the closed position without the use of an adhesive.

Methods of skin tightening described herein can have a visual, detectable, and/or quantifiable reduction of tissue volume and/or skin laxity. Methods described herein can also reduce wrinkles. For instance the effect of a method described herein, in some cases, can be quantified by a point reduction of the Lemperle Assessment Scale, as described for example in Lemperle G, et al., A classification of facial wrinkles. Plast Reconstr Surg. 2001; 108:1735-50. The Lemperle Assessment scale is a semi-quantitative method for assessing pre-auricular wrinkle severity, where 0=No wrinkles; 1=Just perceptible wrinkles; 2=Shallow wrinkles; 3=Moderately deep wrinkles; 4=Deep wrinkles, well-defined edges; 5=Very deep wrinkles, redundant fold. In some embodiments, the methods described herein result in a quantifiable reduction of tissue volume and/or skin laxity and/or degree of wrinkling by 1 to 3 point reduction on the Lemperle Scale. In another embodiments, the methods result in a 1 to 2 point reduction or a 1 point reduction on the Lemperle Scale.

In the embodiments discussed herein, any beneficial area or volumetric fraction of skin can be removed from a treatment area. For example, in some cases, up to 30% of the skin area in a treatment area can be removed. In some instances, between 1% and 25% of the skin area in a treatment area can be removed. In some embodiments between 5% and 20% of the skin area can be removed. In other embodiments between 10% and 20% or between 10% and 15% of the skin area can be removed. In another embodiment, between 15% and 30%, between 15% and 25%, or between 20% and 30% of the skin area can be removed.

The degree of skin tightening or overall skin tightening achieved by the methods described herein is generally related to a total area of the columns of skin removed. In some embodiments, the degree of skin tightening is approximately 1 to 0.5, where removal of 1% of the skin within the treatment area correspondingly results in a 0.5% reduction in the total area of the treatment area. In another embodiment, the degree of skin tightening is approximately 1 to 1, where removal of 1% of the skin within the treatment area correspondingly results in a 1% reduction in the total area of the treatment area. In another embodiment, the degree of skin tightening is approximately 1 to 1.5, where removal of 1% of the skin within the treatment area correspondingly results in a 1.5% reduction in the total area of the treatment area.

II. System for Skin Tightening

In another aspect, systems for skin tightening are described herein, which in some embodiments are capable of performing the methods previously described herein in Section I. Unless expressly stated otherwise, the various components and elements discussed in Section I correspond to the various components and elements described below, such as, for example, the lasers, mechanical excision devices, adhesives, frames, computers and controllers, and the like, and their accompanying descriptions in Section I are incorporated by reference in their entirety herein below.

In an embodiment, the system for skin tightening comprises a laser, an imaging system and/or device, and at least one controller. The laser is configured to fractionally ablate two or more columns of skin from a treatment area on the skin, thereby forming two or more columnar vacancies in the skin, the columnar vacancies each having a perimeter defined by a first side and a second side opposite the first side, the first side and the second side each comprising an epidermal layer, a dermal layer, and a subcutaneous layer of skin. The laser can be a pulsed laser or a continuous wave laser having the physical, optical, and energetic properties previously described above in Section I.

The imaging system is configured to image blood vessels in the treatment area of the skin, and determine locations of substantially non-vascularized areas within the treatment area of the skin based on the blood vessel images. The imaging system can comprise an optical imaging system, such as an optical coherence tomography (OCT) system, a multi-photon imaging system, or a reflectance confocal microscopy (RCM) system, fluorescence spectroscopy system, camera recognition and image processing system, or other optical imaging technology capable of non-invasive imaging of blood vessels in the skin. In an embodiment the imaging system is an OCT system having the components and physical properties previously described above in Section I.

In some embodiments, the imaging system of a device described herein comprises an acoustic imaging system. For instance, in some cases, the imaging system is an ultrasound imaging system comprising one or more ultrasound transducers and/or receivers as commonly known in the art.

Figure 10:
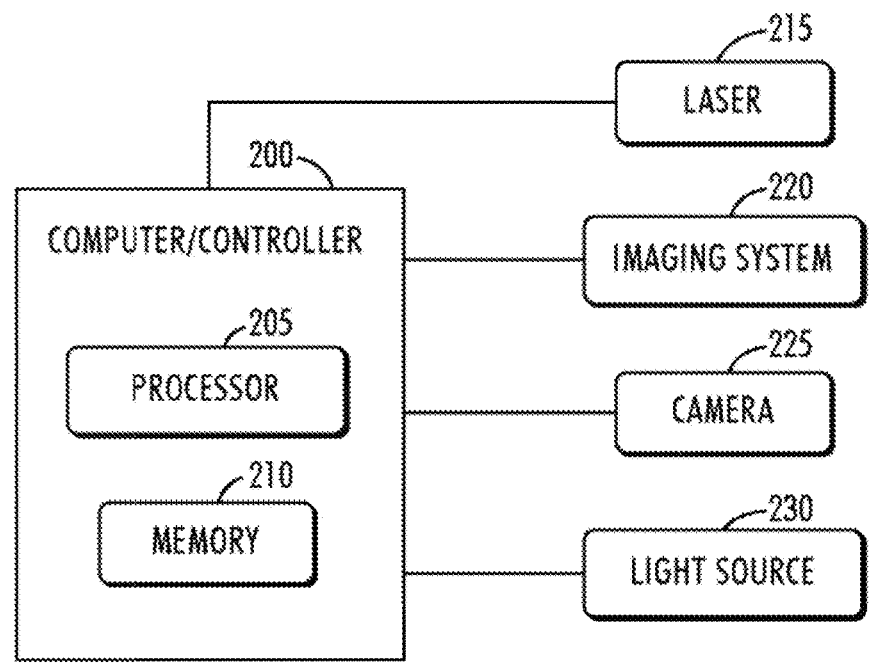
FIG. 10 is a schematic of a computer system and/or controller operatively connected to a laser and an imaging system.

As shown in the embodiment of FIG. 10 and previously discussed in Section I, the computer or controller 200 operatively connected to the laser 215 and the imaging system 220, the computer or controller 200 being configured to automatedly control imaging of the blood vessels in the treatment area, and subsequent fractional laser ablation location in the treatment area. In some embodiments, the computer or controller 200 is configured to automatedly control the fractional laser ablation locations in the treatment area without performing imaging of the blood vessels in the treatment area. The computer or controller 200 can include a processor 205 and a non-transitory memory 210 storing computer-readable program code that, in response to execution by the processor 205, cause instructions to be provided to the laser 215, the imaging system 220, or both in a desired sequence. The computer or controller 200 can be configured to receive, as input, imaging data captured by the imaging system 220 of the blood vessels in the treatment area, and construct a digitized map of the treatment area showing substantially non-vascularized and vascularized regions. In an embodiment, the computer or controller 200 is configured to output (e.g., via a wired or wireless connection) control signals or commands instructing the laser to move to positions or locations relative to the treatment area of the skin that is centered over one of the desired coordinates corresponding to the substantially non-vascularized target locations. Once the laser is in a desired position or configuration, the controller can output control signals or commands instructing the laser to generate an ablative laser beam.

In some embodiments, the system for skin tightening further comprises an adhesive capable of holding the columnar vacancy in a closed position when applied to the skin over the columnar vacancy. The adhesive can comprise a urethane polymer-based adhesive or a cyanoacrylate polymer-based adhesive, such as those described above in Section I, or any other adhesive not inconsistent with the objectives of this disclosure.

In an embodiment, when the adhesive is transparent to light in the infrared and/or visible regions of the spectrum (or another region), the system further comprises a light source capable of generating light that can pass through the applied adhesive and have a therapeutic effect on the columnar vacancy, as described above in Section I. The irradiating light can, in some cases, provide one or more therapeutically beneficial effects. For example, the step of irradiating can cause or contribute to hemostasis, coagulation, or both of the closed columnar vacancy. The irradiative light source can be a non-ablative laser or broad band light ("BBL") source, such as the non-ablative irradiative light sources described above in Section I. In some embodiments, the system laser previously described herein can comprise a hybrid laser operable to produce laser beams having a plurality of differing wavelengths, such that the hybrid laser is capable of performing both fractional laser ablation of the skin at an ablative wavelength, and non-ablative irradiation at a different wavelength.

In addition, in some embodiments, a system described herein further comprises a camera. In some cases, the camera is positioned or configured to receive light from the imaged treatment area, directly or through the use of one or more lenses, mirrors, or apertures. Such light can be the return signal of the imaging device. Moreover, in some embodiments, the camera can be attached to any portion of a system described herein. Any camera not inconsistent with the objectives of the present disclosure may be used. For example, in some cases, the camera comprises a digital camera capable of capturing, recording, and/or processing two-dimensional or three-dimensional images of the treatment area. Further, a camera described herein can be a visible light camera or an infrared camera. Other cameras may also be used. The camera can be operatively connected to the controller/computer 200 controlling the imaging system 220 and laser 215, as shown for example in FIG. 10, and the controller 200 can use imaging data of the treatment area to monitor and record the location of columnar vacancies formed by the laser 215, and to direct, calibrate, or otherwise control the laser 215 with respect to the location of new columnar vacancies to be formed in the treatment area.

Additionally, in some embodiments, the system described herein comprises a light source (other than a laser or BBL described above), as shown for example in FIG. 10 as light source 230. In some instances, the camera described herein can comprise the light source for illuminating an area or surface that is to be imaged and/or treated by the system, or in other instances, the light source can be a separate device. In an embodiment, the light source is operatively controlled by the controller or computer 200. Any light source not inconsistent with the objectives of the present disclosure may be used. For instance, in some cases, the light source comprises or is a non-laser light emitting diode or device (LED). The light source may also be an incandescent or fluorescent light bulb. Other light sources may also be used. Additionally, the light source of an imaging device described herein can be positioned or located on any portion of the imaging device or overall system not inconsistent with the objectives of this disclosure, provided that the light source is capable of illuminating the treatment area.

In some embodiments, the system of skin tightening further comprises a frame capable of closing a columnar vacancy and connecting the first side of the columnar vacancy to the opposing second side of the columnar vacancy. In an embodiment, the frame has the same mechanical, physical, and operable mechanism as the frame 300 previously described above in Section I.

Various components of systems and methods have been described above. It is to be understood that a system or a method described herein can include any combination of features or components described herein not inconsistent with the objectives of this disclosure.

Systems and methods described herein are further illustrated by the non-limiting Examples below.

EXAMPLE 1

Creation of Columnar Vacancy with Fractional Laser Ablation

A diamond-shaped columnar vacancy in skin shown in FIG. 6A was formed using a diamond-shaped cross-sectional laser beam created with a 50 watt Er:YAG laser. The columnar vacancy has an area of 20 mm$^3$ (10 mm overall length, 2 mm overall width, and 2 mm overall depth). To create the columnar vacancy, the Er:YAG laser ablated the skin for one second at a 2.5 joules per mm$^3$ ablation energy density.

EXAMPLE 2

Creation of Columnar Vacancy with Fractional Laser Ablation

A diamond-shaped columnar vacancy in skin shown in FIG. 6B was formed using a diamond-shaped cross-sectional laser beam created with a 50 watt Er:YAG laser. The columnar vacancy has an area of 22.5 mm$^2$ (15 mm overall length and 1.5 mm overall width), with a 1 mm overall depth. To create the columnar vacancy, the Er:YAG laser ablated the skin with 30 pulses at 8.3 J/pulse and a 0.4 joule per mm$^3$ ablation energy density. More particularly, approximately 300 total pulses are used (30 pulses with 10 sub-pulses each), with a total duration of 5-6 seconds.

EXAMPLE 3

Methods of Skin Tightening

Exemplary methods described herein are performed as follows. The methods of this Example, more particularly, use fractional laser ablation and a TEGADERM® or DERMABOND® adhesive. The methods are performed on a treatment area comprising excess brachial skin following laser liposuction. The treatment area has a total area of 400 cm$^2$ (approximately 20 cm overall length and 20 cm overall width). An Er:YAG laser performs fractional ablation on the treatment area, creating 400 columnar vacancies, each columnar vacancy having an area of approximately 0.1 cm$^2$, where a combined area of the 400 columnar vacancies equals approximately 40 cm$^2$, or 10% of the total area of the treatment area. The automated fractional laser ablation forms the 400 columnar vacancies in approximately 400 seconds (approximately 7 minutes). The columnar vacancies are closed using TEGADERM® or DERMABOND®, and the treatment area after healing results in an approximate 10% reduction in area (a 10% shrinkage).

SELECT EMBODIMENTS

Although the above description and the attached claims disclose a number of embodiments of the invention, other aspects of the invention are disclosed in the following further embodiments.

Embodiment 1. A method of closing a wound on a surface of skin, the method comprising:
  attaching a frame, in an open position, to the surface of the skin, wherein the frame surrounds the wound, the wound having a perimeter defined by a first side and a second side opposite the first side, the first side and the second side each comprising an epidermal layer, a dermal layer, and a subcutaneous layer of skin; and
  altering the shape of the frame, while the frame is attached to the surface of the skin, from an open shape of the open position of the frame to a closed shape of a closed position of the frame,
  wherein altering the shape of the frame from the open shape to the closed shape connects the first side of the wound to the second side of the wound, and
  wherein the epidermal layer, the dermal layer, and/or the subcutaneous layer of the first side of the wound is aligned, respectively, with the epidermal layer, the dermal layer, and/or the subcutaneous layer of the second side of the wound in a z-direction orthogonal to the surface of the skin, when the frame is in the closed position.

Embodiment 2. The method of embodiment 1 further comprising retaining the frame in the closed position on the surface of the skin during healing of the wound.

Embodiment 3. The method of embodiment 2 further comprising removing the frame from the surface of the skin following healing of the wound.

Embodiment 4. The method of embodiment 1, wherein the frame is formed from metal, plastic, or a composite material.

Embodiment 5. The method of embodiment 1, wherein the frame comprises two or more hinges defining two or more corners of the frame in the open position.

Embodiment 6. The method of embodiment 5, wherein altering the shape of the frame from the open shape to the closed shape comprises closing the hinges of the frame to reduce the angles defined by the corners of the frame.

Embodiment 7. The method of embodiment 1, wherein the open shape of the frame is a polygonal shape having an open internal area defined by edges of the frame.

Embodiment 8. The method of embodiment 7, wherein the open shape of the frame is a diamond shape.

Embodiment 9. The method of embodiment 7, wherein the closed shape of the frame is a generally arcuate or linear shape having a closed internal area defined by edges of the frame.

Embodiment 10. The method of embodiment 1, wherein alignment of the epidermal layers, the dermal layers, and/or the subcutaneous layers of the first and second sides of the wound is provided by an inability of the frame to distort substantially in the z-direction during altering of the shape of the frame from the open shape to the closed shape.

Embodiment 11. The method of embodiment 10, wherein the inability of the frame to distort substantially is provided by one or more tabs of the frame.

Embodiment 12. The method of embodiment 10, wherein the inability of the frame to distort substantially is provided by an external apparatus used to alter the shape of the frame from the open shape to the closed shape.

Embodiment 13. The method of embodiment 1, wherein the epidermal layers, the dermal layers, and/or the subcutaneous layers of the first and second sides of the wound are substantially relaxed or untensioned when the frame is in the closed position.

Embodiment 14. The method of embodiment 1, wherein the epidermal layers, the dermal layers, and the subcutaneous layers of the first and second sides of the wound are aligned to form a substantially planar and untensioned dermal-epidermal junction and a substantially planar and untensioned dermal-subcutaneous junction across the first and second sides of the wound, when the frame is in the closed position.

Embodiment 15. The method of embodiment 1, wherein the frame includes one or more pins, staples, or anchors extending downwardly into a dermal or subcutaneous layer of the skin from a bottom of the frame that is in contact with and adhered to the surface of the skin.

Embodiment 16. The method of embodiment 1, wherein the frame is adhered to the surface of the skin with an adhesive.

Embodiment 17. A system for closing a wound on a surface of skin, the system comprising:
  a deformable frame configured to have an open shape in an open position and a closed shape in a closed position when attached to the surface of the skin, wherein, in the open position, the frame is configured to surround the wound, the wound having a perimeter defined by a first side and a second side opposite the first side, the first side and the second side each comprising an epidermal layer, a dermal layer, and a subcutaneous layer of skin;
  wherein, in the closed position, the frame is configured to connect the first side of the wound to the second side of the wound; and
wherein the epidermal layer, the dermal layer, and/or the subcutaneous layer of the first side of the wound is aligned, respectively, with the epidermal layer, the dermal layer, and/or the subcutaneous layer of the second side of the wound in a z-direction orthogonal to the surface of the skin, when the frame is in the closed position.

Embodiment 18. The system of embodiment 17 further comprising an apparatus configured to alter the shape of the frame from the open shape to the closed shape.

Embodiment 19. The system of embodiment 17, wherein the frame is formed from metal, plastic, or a composite material.

Embodiment 20. The system of embodiment 17, wherein the frame comprises two or more hinges defining two or more corners of the frame in the open position.

Embodiment 21. The system of embodiment 17, wherein the open shape of the frame is a polygonal shape having an open internal area defined by edges of the frame.

Embodiment 22. The system of embodiment 21, wherein the open shape of the frame is a diamond shape.

Embodiment 23. The system of embodiment 21, wherein the closed shape of the frame is a generally arcuate or linear shape having a closed internal area defined by edges of the frame.

Embodiment 24. The system of embodiment 17, wherein the frame is unable to distort substantially in the z-direction during altering of the shape of the frame from the open shape to the closed shape.

Embodiment 25. The system of embodiment 24, wherein the frame comprises one or more tabs, and the tabs prevent the frame from distorting substantially in the z-direction during altering of the shape of the frame from the open shape to the closed shape.

Embodiment 26. The system of embodiment 24, wherein the system further comprises an apparatus configured to alter the shape of the frame from the open shape to the closed shape, and the apparatus is configured to prevent the frame from distorting substantially in the z-direction during altering of the shape of the frame from the open shape to the closed shape.

Embodiment 27. The system of embodiment 17, wherein the epidermal layers, the dermal layers, and/or the subcutaneous layers of the first and second sides of the wound are substantially relaxed or untensioned when the frame is in the closed position.

Embodiment 28. The system of embodiment 17, wherein the epidermal layers, the dermal layers, and the subcutaneous layers of the first and second sides of the wound are aligned to form a substantially planar and untensioned dermal-epidermal junction and a substantially planar and untensioned dermal-subcutaneous junction across the first and second sides of the wound, when the frame is in the closed position.

Embodiment 29. The system of embodiment 17, wherein the frame includes one or more pins, staples, or anchors extending downwardly into a dermal or subcutaneous layer of the skin from a bottom of the frame that is in contact with and adhered to the surface of the skin.

Embodiment 30. The system of embodiment 17, wherein the frame is adhered to the surface of the skin with an adhesive.

Embodiment 31. A method of tightening skin, the method comprising:
- attaching a frame, in an open position, to the surface of the skin, wherein the frame surrounds a treatment area of the skin;
- removing one or more columns of skin from the treatment area, thereby forming one or more columnar vacancies in the skin, the columnar vacancies each having a perimeter defined by a first side and a second side opposite the first side, the first side and the second side each comprising an epidermal layer, a dermal layer, and a subcutaneous layer of skin; and
- altering the shape of the frame, while the frame is attached to the surface of the skin, from an open shape of the open position of the frame to a closed shape of a closed position of the frame,
- wherein altering the shape of the frame from the open shape to the closed shape connects the first side of at least one of the one or more columnar vacancies to the second side of the at least one columnar vacancy, and
- wherein the epidermal layer, the dermal layer, and/or the subcutaneous layer of the first side of the columnar vacancy is aligned, respectively, with the epidermal layer, the dermal layer, and/or the subcutaneous layer of the second side of the columnar vacancy in a z-direction orthogonal to the surface of the skin, when the frame is in the closed position.

Embodiment 32. The method of embodiment 31 further comprising retaining the frame in the closed position on the surface of the skin during healing and closure of the columnar vacancy.

Embodiment 33. The method of embodiment 32 further comprising removing the frame from the surface of the skin following healing and closure of the columnar vacancy.

Embodiment 34. The method of embodiment 31, wherein the frame is formed from metal, plastic, or a composite material.

Embodiment 35. The method of embodiment 31, wherein the frame comprises two or more hinges defining two or more corners of the frame in the open position.

Embodiment 36. The method of embodiment 35, wherein altering the shape of the frame from the open shape to the closed shape comprises closing the hinges of the frame to reduce the angles defined by the corners of the frame.

Embodiment 37. The method of embodiment 31, wherein the open shape of the frame is a polygonal shape having an open internal area defined by edges of the frame.

Embodiment 38. The method of embodiment 37, wherein the open shape of the frame is a diamond shape.

Embodiment 39. The method of embodiment 37, wherein the closed shape of the frame is a generally arcuate or linear shape having a closed internal area defined by edges of the frame.

Embodiment 40. The method of embodiment 31, wherein alignment of the epidermal layers, the dermal layers, and/or the subcutaneous layers of the first and second sides of the columnar vacancy is provided by an inability of the frame to distort substantially in the z-direction during altering of the shape of the frame from the open shape to the closed shape.

Embodiment 41. The method of embodiment 40, wherein the inability of the frame to distort substantially in the z-direction is provided by one or more tabs of the frame.

Embodiment 42. The method of embodiment 40, wherein the inability of the frame to distort substantially in the z-direction is provided by an external apparatus used to alter the shape of the frame from the open shape to the closed shape.

Embodiment 43. The method of embodiment 31, wherein the epidermal layers, the dermal layers, and/or the subcutaneous layers of the first and second sides of the columnar vacancy are substantially relaxed or untensioned when the frame is in the closed position.

Embodiment 44. The method of embodiment 31, wherein the epidermal layers, the dermal layers, and the subcutaneous layers of the first and second sides of the columnar vacancy are aligned to form a substantially planar and untensioned dermal-epidermal junction and a substantially planar and untensioned dermal-subcutaneous junction across the first and second sides of the columnar vacancy, when the frame is in the closed position.

Embodiment 45. The method of embodiment 31, wherein the frame includes one or more pins, staples, or anchors extending downwardly into a dermal or subcutaneous layer of the skin from a bottom of the frame that is in contact with and adhered to the surface of the skin.

Embodiment 46. The method of embodiment 41, wherein the frame is adhered to the surface of the skin with an adhesive.

Embodiment 47. The method of embodiment 31, wherein removing one or more columns of skin from the treatment area comprises ablating the one or more columns of skin with a laser.

Embodiment 48. The method of embodiment 47, wherein the laser is an Er:YAG laser.

Embodiment 49. The method of embodiment 31, wherein removing one or more columns of skin from the treatment area comprises physically coring the one or more columns of skin with a coring apparatus.

Embodiment 50. The method of embodiment 31, wherein the columns of skin are cylindrical columns of skin.

Embodiment 51. The method of embodiment 31, wherein the columns of skin are polygon-shaped columns of skin.

Embodiment 52. The method of embodiment 31, wherein the columns of skin are diamond-shaped columns of skin.

Embodiment 53. A system for tightening skin, the system comprising:
- a deformable frame configured to have an open shape in an open position and a closed shape in a closed position when attached to a surface of the skin, wherein, in the open position, the frame is configured to surround a treatment area of the skin; and
- a laser configured to remove one or more columns of skin from the treatment area, thereby forming one or more columnar vacancies in the skin, the columnar vacancies each having a perimeter defined by a first side and a second side opposite the first side, the first side and the second side each comprising an epidermal layer, a dermal layer, and a subcutaneous layer of skin,
- wherein, in the closed position, the frame is configured to connect the first side of at least one of the columnar vacancies to the second side of the at least one columnar vacancy; and wherein the epidermal layer, the dermal layer, and/or the subcutaneous layer of the first side of the columnar vacancy is aligned, respectively, with the epidermal layer, the dermal layer, and/or the subcutaneous layer of the second side of the columnar vacancy in a z-direction orthogonal to the surface of the skin, when the frame is in the closed position.

Embodiment 54. The system of embodiment 53 further comprising an apparatus configured to alter the shape of the frame from the open shape to the closed shape.

Embodiment 55. The system of embodiment 53, wherein the frame is formed from metal, plastic, or a composite material.

Embodiment 56. The system of embodiment 53, wherein the frame comprises two or more hinges defining two or more corners of the frame in the open position.

Embodiment 57. The system of embodiment 53, wherein the open shape of the frame is a polygonal shape having an open internal area defined by edges of the frame.

Embodiment 58. The system of embodiment 57, wherein the open shape of the frame is a diamond shape.

Embodiment 59. The system of embodiment 57, wherein the closed shape of the frame is a generally arcuate or linear shape having a closed internal area defined by edges of the frame.

Embodiment 60. The system of embodiment 53, wherein the frame is unable to distort substantially in the z-direction during altering of the shape of the frame from the open shape to the closed shape.

Embodiment 61. The system of embodiment 60, wherein the frame comprises one or more tabs, and the tabs prevent the frame from distorting substantially in the z-direction during altering of the shape of the frame from the open shape to the closed shape.

Embodiment 62. The system of embodiment 60, wherein the system further comprises an apparatus configured to alter the shape of the frame from the open shape to the closed shape, and the apparatus is configured to prevent the frame from distorting substantially in the z-direction during altering of the shape of the frame from the open shape to the closed shape.

Embodiment 63. The system of embodiment 53, wherein the epidermal layers, the dermal layers, and/or the subcutaneous layers of the first and second sides of the columnar vacancy are substantially relaxed or untensioned when the frame is in the closed position.

Embodiment 64. The system of embodiment 53, wherein the epidermal layers, the dermal layers, and the subcutaneous layers of the first and second sides of the columnar vacancy are aligned to form a substantially planar and untensioned dermal-epidermal junction and a substantially planar and untensioned dermal-subcutaneous junction across the first and second sides of the columnar vacancy, when the frame is in the closed position.

Embodiment 65. The system of embodiment 53, wherein the frame includes one or more pins, staples, or anchors extending downwardly into a dermal or subcutaneous layer of the skin from a bottom of the frame that is in contact with and adhered to the surface of the skin.

Embodiment 66. The system of embodiment 53, wherein the frame is adhered to the surface of the skin with an adhesive.

Embodiment 67. The system of embodiment 53, wherein the laser is an Er:YAG laser.

Embodiment 68. A method of removing a scar from skin, the method comprising attaching a frame, in an open position, to the surface of the skin, wherein the frame surrounds at least a portion of the scar;

removing skin tissue forming the scar, thereby forming a wound in the skin, the wound having a perimeter defined by a first side and a second side opposite the first side, the first side and the second side each comprising an epidermal layer, a dermal layer, and a subcutaneous layer of skin; and altering the shape of the frame, while the frame is attached to the surface of the skin, from an open shape of the open position of the frame to a closed shape of a closed position of the frame, wherein altering the shape of the frame from the open shape to the closed shape connects the first side of the wound to the second side of the wound, and wherein the epidermal layer, the dermal layer, and/or the subcutaneous layer of the first side of the wound is aligned, respectively, with the epidermal layer, the dermal layer, and/or the subcutaneous layer of the second side of the wound in a z-direction orthogonal to the surface of the skin, when the frame is in the closed position.

Embodiment 69. The method of embodiment 68 further comprising retaining the frame in the closed position on the surface of the skin during healing and closure of the wound.

Embodiment 70. The method of embodiment 69 further comprising removing the frame from the surface of the skin following healing and closure of the wound.

Embodiment 71. The method of embodiment 68, wherein the frame is formed from metal, plastic, or a composite material.

Embodiment 72. The method of embodiment 68, wherein the frame comprises two or more hinges defining two or more corners of the frame in the open position.

Embodiment 73. The method of embodiment 72, wherein altering the shape of the frame from the open shape to the closed shape comprises closing the hinges of the frame to reduce the angles defined by the corners of the frame.

Embodiment 74. The method of embodiment 68, wherein the open shape of the frame is a polygonal shape having an open internal area defined by edges of the frame.

Embodiment 75. The method of embodiment 74, wherein the open shape of the frame is a diamond shape.

Embodiment 76. The method of embodiment 74, wherein the closed shape of the frame is a generally arcuate or linear shape having a closed internal area defined by edges of the frame.

Embodiment 77. The method of embodiment 68, wherein alignment of the epidermal layers, the dermal layers, and/or the subcutaneous layers of the first and second sides of the wound is provided by an inability of the frame to distort substantially in the z-direction during altering of the shape of the frame from the open shape to the closed shape.

Embodiment 78. The method of embodiment 77, wherein the inability of the frame to distort substantially in the z-direction is provided by one or more tabs of the frame.

Embodiment 79. The method of embodiment 77, wherein the inability of the frame to distort substantially in the z-direction is provided by an external apparatus used to alter the shape of the frame from the open shape to the closed shape.

Embodiment 80. The method of embodiment 68, wherein the epidermal layers, the dermal layers, and/or the subcutaneous layers of the first and second sides of the wound are substantially relaxed or untensioned when the frame is in the closed position.

Embodiment 81. The method of embodiment 68, wherein the epidermal layers, the dermal layers, and the subcutaneous layers of the first and second sides of the wound are aligned to form a substantially planar and untensioned dermal-epidermal junction and a substantially planar and untensioned dermal-subcutaneous junction across the first and second sides of the wound, when the frame is in the closed position.

Embodiment 82. The method of embodiment 68, wherein the frame includes one or more pins, staples, or anchors extending downwardly into a dermal or subcutaneous layer of the skin from a bottom of the frame that is in contact with and adhered to the surface of the skin.

Embodiment 83. The method of embodiment 68, wherein the frame is adhered to the surface of the skin with an adhesive.

Embodiment 84. The method of embodiment 68, wherein ablating the skin tissue forming the scar is performed with a laser.

Embodiment 85. The method of embodiment 84, wherein the laser is an Er:YAG laser.

Embodiment 86. The method of embodiment 84, wherein the step of ablating the skin tissue forming the scar with a laser is an automated step.

Embodiment 87. The method of embodiment 86, wherein the automated ablation step is carried out using a computer controller and an imaging system configured to image the scar and/or the frame surrounding at least a portion of the scar.

Embodiment 88. A system for removing a scar, the system comprising:
  a deformable frame configured to have an open shape in an open position and a closed shape in a closed position when attached to the surface of the skin, wherein, in the open position, the frame is configured to surround at least a portion of the scar; and
  a laser configured to remove skin tissue forming the scar, thereby forming a wound in the skin, the wound having a perimeter defined by a first side and a second side opposite the first side, the first side and the second side each comprising an epidermal layer, a dermal layer, and a subcutaneous layer of skin,
  wherein, in the closed position, the frame is configured to connect the first side of the wound to the second side of the wound; and
wherein the epidermal layer, the dermal layer, and/or the subcutaneous layer of the first side of the wound is aligned, respectively, with the epidermal layer, the dermal layer, and/or the subcutaneous layer of the second side of the wound in a z-direction orthogonal to the surface of the skin, when the frame is in the closed position.

Embodiment 89. The system of embodiment 88 further comprising an apparatus configured to alter the shape of the frame from the open shape to the closed shape.

Embodiment 90. The system of embodiment 88, wherein the frame is formed from metal, plastic, or a composite material.

Embodiment 91. The system of embodiment 88, wherein the frame comprises two or more hinges defining two or more corners of the frame in the open position.

Embodiment 92. The system of embodiment 88, wherein the open shape of the frame is a polygonal shape having an open internal area defined by edges of the frame.

Embodiment 93. The system of embodiment 88, wherein the open shape of the frame is a diamond shape.

Embodiment 94. The system of embodiment 88, wherein the closed shape of the frame is a generally arcuate or linear shape having a closed internal area defined by edges of the frame.

Embodiment 95. The system of embodiment 88, wherein the frame is unable to distort substantially in the z-direction during altering of the shape of the frame from the open shape to the closed shape.

Embodiment 96. The system of embodiment 95, wherein the frame comprises one or more tabs, and the tabs prevent the frame from distorting substantially in the z-direction during altering of the shape of the frame from the open shape to the closed shape.

Embodiment 97. The system of embodiment 95, wherein the system further comprises an apparatus configured to alter the shape of the frame from the open shape to the closed shape, and the apparatus is configured to prevent the frame from distorting substantially in the z-direction during altering of the shape of the frame from the open shape to the closed shape.

Embodiment 98. The system of embodiment 88, wherein the epidermal layers, the dermal layers, and/or the subcutaneous layers of the first and second sides of the wound are substantially relaxed or untensioned when the frame is in the closed position.

Embodiment 99. The system of embodiment 88, wherein the epidermal layers, the dermal layers, and the subcutaneous layers of the first and second sides of the wound are aligned to form a substantially planar and untensioned dermal-epidermal junction and a substantially planar and untensioned dermal-subcutaneous junction across the first and second sides of the columnar vacancy, when the frame is in the closed position.

Embodiment 100. The system of embodiment 88, wherein the frame includes one or more pins, staples, or anchors extending downwardly into a dermal or subcutaneous layer of the skin from a bottom of the frame that is in contact with and adhered to the surface of the skin.

Embodiment 101. The system of embodiment 88, wherein the laser is an Er:YAG laser.

Embodiment 102. A method for tightening skin, the method comprising ablating one or more columns of skin from a treatment area on the surface of the skin, wherein the one or more columns of skin are ablated with a laser beam having a polygonal cross-section.

Embodiment 103. The method of embodiment 102, wherein the laser beam has a diamond-shaped cross-section.

Embodiment 104. The method of embodiment 102, wherein ablating the one or more columns of skin forms one or more columnar vacancies in the skin, the columnar vacancies each having a perimeter defined by a first side and a second side opposite the first side, the first side and the second side each comprising an epidermal layer, a dermal layer, and a subcutaneous layer of skin.

Embodiment 105. The method of embodiment 104 further comprising applying a compressive force to the one or more columnar vacancies during healing of the one or more columnar vacancies.

Embodiment 106. The method of embodiment 105, wherein the compressive force is applied using a frame, dermal bond material, stitch, staple, or directional bandage.

Embodiment 107. The method of embodiment 102, wherein the ablating step is carried out using an Er:YAG laser.

Embodiment 108. A system for tightening skin, the system comprising a laser configured to ablate one or more columns of skin from a treatment area on the surface of the skin, thereby forming one or more columnar vacancies in the skin, the columnar vacancies each having a perimeter defined by a first side and a second side opposite the first side, the first side and the second side each comprising an epidermal layer, a dermal layer, and a subcutaneous layer of skin, wherein the laser produces a laser beam having a polygonal cross-section.

Embodiment 109. The system of embodiment 108, wherein the laser beam has a diamond-shaped cross-section.

Embodiment 110. The system of embodiment 108 further comprising a means for applying a compressive force to the one or more columnar vacancies during healing of the one or more columnar vacancies.

Embodiment 111. The system of embodiment 110, wherein the means comprises a frame, dermal bond material, stitch, staple, or directional bandage.

Embodiment 112. The system of embodiment 108, wherein the laser is an Er:YAG laser.

Various embodiments of the invention have been described in fulfillment of the various objectives of the invention. It should be recognized that these embodiments are merely illustrative of the principles of the invention. Numerous modifications and adaptations thereof will be readily apparent to those skilled in the art without departing from the spirit and scope of the invention.

The invention claimed is:

1. A method of tightening skin, comprising:
    performing a fractional laser ablation in a treatment area of the skin, thereby removing a column of the skin and forming a columnar vacancy in the skin, the columnar vacancy having a perimeter defined by a first side and a second side opposite the first side, the first side and the second side each comprising an epidermal layer, a dermal layer, and a subcutaneous layer of skin;
    contacting the first side of the columnar vacancy to the second side of the columnar vacancy, thereby closing the columnar vacancy;
    applying an adhesive to the skin over the closed columnar vacancy, and
    irradiating the closed columnar vacancy with a laser or broad band light through the applied adhesive;
    wherein the epidermal layer, the dermal layer, and the subcutaneous layer of the first side of the columnar vacancy is aligned, respectively, with the epidermal layer, the dermal layer, and the subcutaneous layer of the second side of the columnar vacancy in a z-direction orthogonal to the surface of the skin and wherein the epidermal layers, the dermal layers, and the subcutaneous layers of the first and second sides of the columnar vacancy are aligned to form a substantially planar dermal-epidermal junction and a substantially planar dermal-subcutaneous junction across the first and second sides of the columnar vacancy when the columnar vacancies are closed.

2. The method of claim 1, further comprising imaging blood vessels in the treatment area prior to performing the fractional laser ablation, thereby forming a map of the vascularized and non-vascularized regions in the treatment area.

3. The method of claim 2, wherein a plurality of columns of skin are removed during fractional laser ablation, forming a plurality of columnar vacancies in the treatment area of the skin.

4. The method of claim 3, wherein the fractional laser ablation is performed substantially on the non-vascularized regions.

5. The method of claim 4, wherein the fractional laser ablation and imaging of blood vessels is automated.

6. The method of claim 5, wherein the automated fractional laser ablation and imaging of blood vessels is carried out using a computer controller operatively connected to a laser and an imager.

7. The method of claim 1, wherein a laser beam used to carry out the fractional laser ablation has a polygonal, diamond-shaped, or ellipse-shaped cross-section.

8. The method of claim 1, wherein a laser beam used to carry out the fractional laser ablation has an ellipse-shaped cross-section.

9. The method of claim 1, wherein the columnar vacancy has an overall length and an overall width, the overall length being 2.5 to 3.5 times greater than the overall width.

10. The method of claim 1, wherein the step of irradiating causes hemostasis, coagulation, or both of the closed columnar vacancy.

11. The method of claim 1, wherein the adhesive applies a compressive force to the closed columnar vacancies.

12. The method of claim 1, wherein the fractional laser ablation is carried out with an Er:YAG laser.

13. A method of tightening skin, the method comprising:
    attaching a frame, in an open position, to the surface of the skin, wherein the frame surrounds a treatment area of the skin;
    removing a column of skin from the treatment area by ablating the skin with a laser, thereby forming a columnar vacancy in the skin, the columnar vacancy having a perimeter defined by a first side and a second side opposite the first side, the first side and the second side each comprising an epidermal layer, a dermal layer, and a subcutaneous layer of skin; and
    altering the shape of the frame, while the frame is attached to the surface of the skin, from an open shape of the open position of the frame to a closed shape of a closed position of the frame,
    wherein altering the shape of the frame from the open shape to the closed shape connects the first side of the columnar vacancies to the second side of the columnar vacancy, and
    wherein the epidermal layer, the dermal layer, and/or the subcutaneous layer of the first side of the columnar vacancy is aligned, respectively, with the epidermal layer, the dermal layer, and/or the subcutaneous layer of the second side of the columnar vacancy in a z-direction orthogonal to the surface of the skin, when the frame is in the closed position.

14. The method of claim 13, further comprising:
    retaining the frame in the closed position on the surface of the skin during healing of the columnar vacancy; and
    removing the frame from the surface of the skin following healing of the columnar vacancy.

15. The method of claim 13, wherein the frame comprises two or more hinges defining two or more corners of the frame in the open position, and altering the shape of the frame from the open shape to the closed shape comprises closing the hinges of the frame to reduce the angles defined by the corners of the frame.

* * * * *